(12) United States Patent
Zhu et al.

(10) Patent No.: US 12,391,560 B2
(45) Date of Patent: Aug. 19, 2025

(54) SILICA-ALUMINA MATERIAL CONTAINING LAMELLAR STRUCTURE, ITS PREPARATION AND APPLICATION THEREOF

(71) Applicants: CHINA PETROLEUM & CHEMICAL CORPORATION, Beijing (CN); SINOPEC DALIAN RESEARCH INSTITUTE OF PETROLEUM AND PETROCHEMICALS CO., LTD., Liaoning (CN)

(72) Inventors: Huihong Zhu, Liaoning (CN); Tiebin Liu, Liaoning (CN); Hao Jin, Liaoning (CN); Yiming Shi, Liaoning (CN); Zhenhui Lv, Liaoning (CN); Guang Yang, Liaoning (CN); Lu Liu, Liaoning (CN); Tao Yang, Liaoning (CN)

(73) Assignees: CHINA PETROLEUM & CHEMICAL CORPORATION, Beijing (CN); SINOPEC DALIAN RESEARCH INSTITUTE OF PETROLEUM AND PETROCHEMICALS CO., LTD., Liaoning (CN)

( * ) Notice: Subject to any disclaimer, the term of this patent is extended or adjusted under 35 U.S.C. 154(b) by 286 days.

(21) Appl. No.: 18/256,941

(22) PCT Filed: Jan. 11, 2022

(86) PCT No.: PCT/CN2022/071289
§ 371 (c)(1),
(2) Date: Jun. 12, 2023

(87) PCT Pub. No.: WO2022/148474
PCT Pub. Date: Jul. 14, 2022

(65) Prior Publication Data
US 2024/0033715 A1   Feb. 1, 2024

(30) Foreign Application Priority Data

Jan. 11, 2021 (CN) .......................... 202110029957.9
Jan. 11, 2021 (CN) .......................... 202110029972.3

(51) Int. Cl.
*C01B 33/26* (2006.01)
*B01J 21/12* (2006.01)
(Continued)

(52) U.S. Cl.
CPC ............... *C01B 33/26* (2013.01); *B01J 21/12* (2013.01); *B01J 27/19* (2013.01); *B01J 35/50* (2024.01);
(Continued)

(58) Field of Classification Search
None
See application file for complete search history.

(56) References Cited

U.S. PATENT DOCUMENTS

| 4,001,144 A | 1/1977 | Pearson et al. |
| 4,683,217 A * | 7/1987 | Lok .......................... C07C 5/02 |
| | | 423/306 |

(Continued)

FOREIGN PATENT DOCUMENTS

| CN | 1723082 A | 1/2006 |
| CN | 103191773 A | 7/2013 |

(Continued)

*Primary Examiner* — In Suk C Bullock
*Assistant Examiner* — Alyssa L Cepluch
(74) *Attorney, Agent, or Firm* — NKL Law; Allen Xue

(57) ABSTRACT

A silica-alumina material, its preparation and application thereof are provided. The silica-alumina material has a $SiO_2/Al_2O_3$ molar ratio of 0.8-1.5, and has a lamellar structure with an average length of 0.5-2 μm and an average thickness of 30-80 nm, and its calcined form has a specific XRD pattern. The silica-alumina material has the characteristics of large pore volume, two-stage gradient pore channels (Continued)

of mesopores and macropores, as well as high B acid content as in molecular sieve, and shows crystal characteristics of a molecular sieve, and low impurity content, and thus is suitable for use as a carrier for catalytic materials, particularly a carrier for heavy oil hydrogenation catalysts.

25 Claims, 3 Drawing Sheets

(51) Int. Cl.

| | | |
|---|---|---|
| *B01J 27/19* | (2006.01) | |
| *B01J 35/50* | (2024.01) | |
| *B01J 35/61* | (2024.01) | |
| *B01J 35/63* | (2024.01) | |
| *B01J 37/02* | (2006.01) | |
| *B01J 37/08* | (2006.01) | |
| *C07C 5/02* | (2006.01) | |
| *B01J 35/70* | (2024.01) | |

(52) U.S. Cl.
CPC ........... *B01J 35/615* (2024.01); *B01J 35/635* (2024.01); *B01J 37/0201* (2013.01); *B01J 37/0236* (2013.01); *B01J 37/088* (2013.01); *C07C 5/02* (2013.01); *B01J 35/70* (2024.01); *B01J 2235/15* (2024.01)

(56) References Cited

U.S. PATENT DOCUMENTS

| | | |
|---|---|---|
| 2004/0092390 A1 | 5/2004 | Timken |
| 2018/0021728 A1 | 1/2018 | Curulla-Ferre et al. |

FOREIGN PATENT DOCUMENTS

| | | |
|---|---|---|
| CN | 105056928 B | 2/2018 |
| CN | 105709789 B | 7/2018 |
| CN | 108499554 A | 9/2018 |
| CN | 108786926 A | 11/2018 |
| CN | 108927128 A | 12/2018 |
| CN | 108927208 A | 12/2018 |
| CN | 108940351 A | 12/2018 |
| CN | 109305689 A | 2/2019 |
| CN | 109833899 A | 6/2019 |
| RU | 2197424 C1 | 1/2003 |
| RU | 2493909 C2 | 9/2013 |
| TW | I372080 B | 9/2012 |

\* cited by examiner

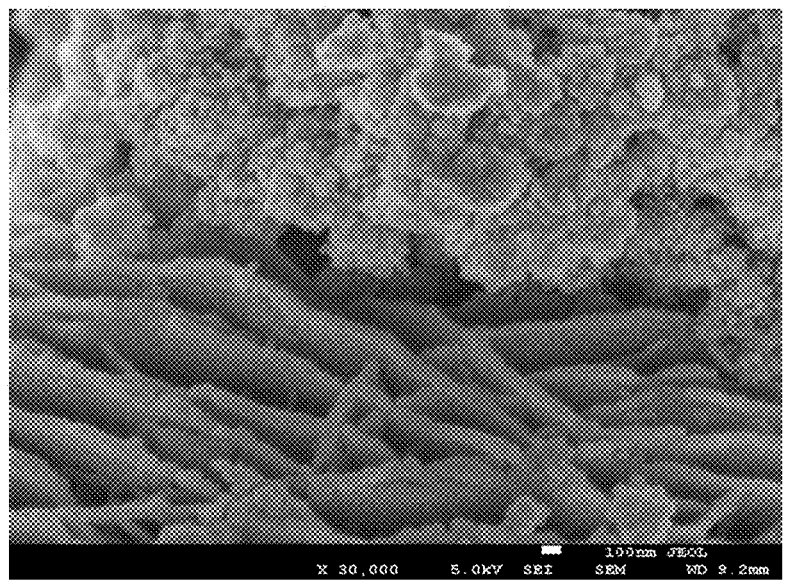
FIG. 1
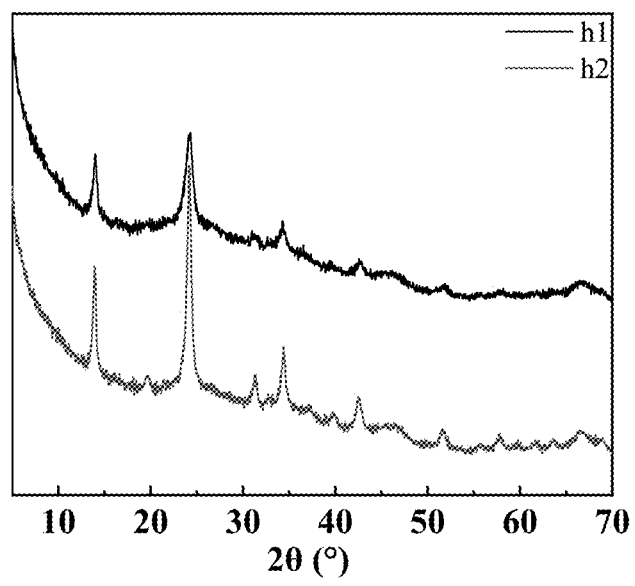
FIG. 2 (h2>h1)

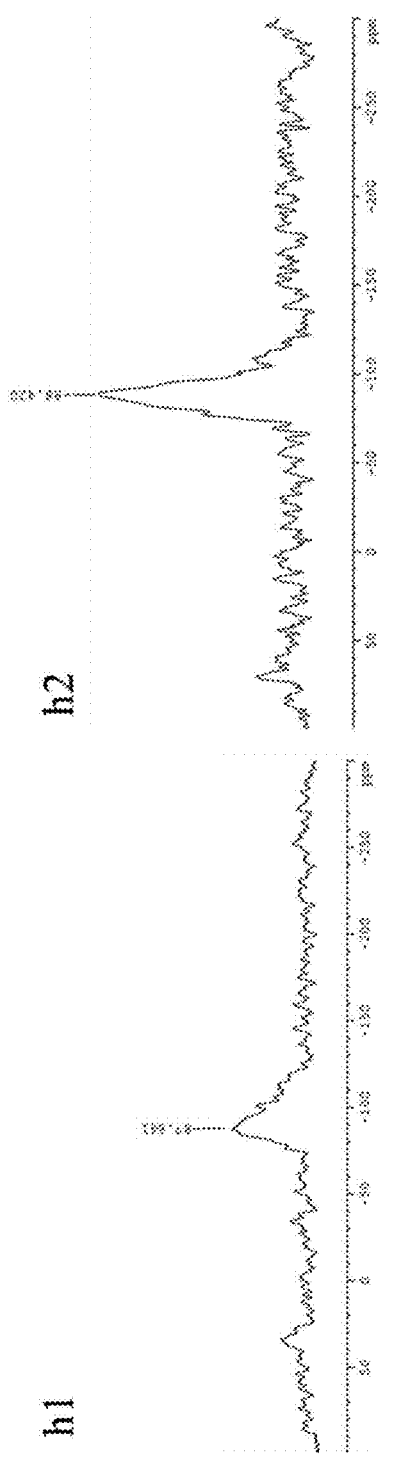
FIG. 3 (h2>h1)
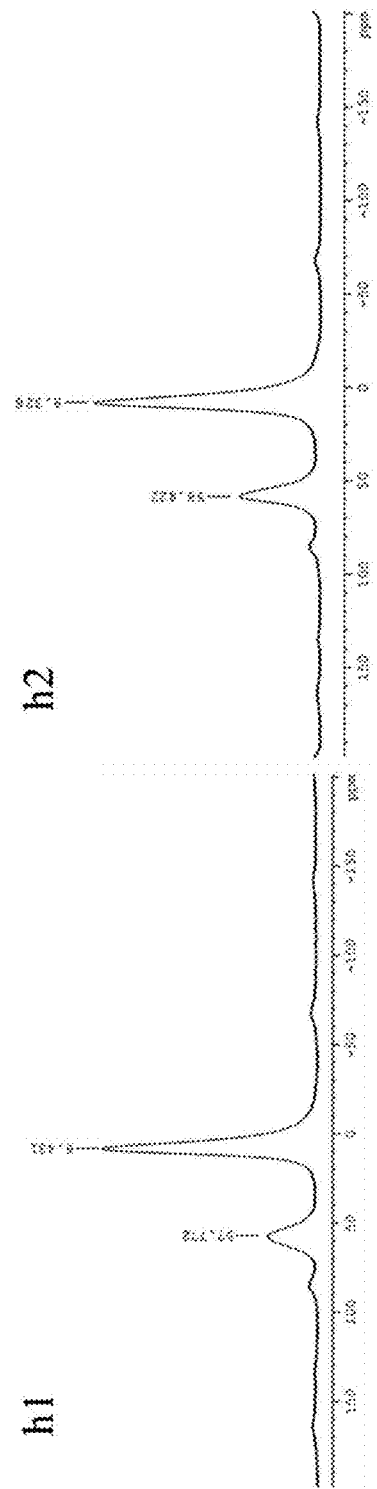
FIG. 4 (h2>h1)

SILICA-ALUMINA MATERIAL CONTAINING LAMELLAR STRUCTURE, ITS PREPARATION AND APPLICATION THEREOF

TECHNICAL FIELD

The present application belongs to the field of catalytic materials, and relates to a silica-alumina material, its preparation and application thereof.

BACKGROUND ART

The hydrocracking catalyst carrier is introduced with molecular sieve to raise the cracking performance of the catalyst. However, as the residue feedstock has the characteristics of large molecules, high nitrogen content and the like, the problems of rapid deactivation and the like easily occur when a molecular sieve catalyst is used, and the application of the molecular sieve catalyst in residue hydrocracking process is limited. Macroporous silica-alumina materials have a proper pore structure and acidity, good hydrothermal stability and strong cracking performance, and are particularly suitable for a residue hydrocracking process.

Methods for producing silica-alumina materials typically include sol-gel method, kneading method, impregnation method, and the like. Macroporous silica-alumina materials are typically made by sol-gel method, which typically uses sodium silicate or silica sol as a silicon source. The difficulty in the production of macroporous silica-alumina material is that with the increase of silica content, the pore volume of the silica-alumina material is gradually reduced, while the sodium content is remarkably increased. Sodium is present as an impurity of the silica-alumina material and needs to be removed, and the sodium content is typically required to be less than 0.5%. Normally, more expensive silica sol is used as a silicon source in industry to reduce the frequency of subsequent sodium removal by washing, or ion exchange is used to remove sodium, but the sodium removal methods greatly increase the production cost of silica-alumina materials and have poor economical efficiency, which limits the large-scale industrial popularization and application of those methods.

CN201710382457.7 discloses a high-activity silica-alumina material and its preparation. The active silica-alumina material comprises 15-45 wt % of silicon and 55-85 wt % of aluminum, calculated as oxides. It has a total BET specific surface area of 300-500 m$^2$/g, a proportion of the micropore specific surface area to the total BET specific surface area of not more than 8%, and an average pore diameter of 5-18 nm; and where c represents the Al/Si atomic ratio of the surface of the material measured by the XPS method, and d represents the Al/Si atomic ratio of the bulk phase of the material measured by the XRF method, c/d=1.2-1.9.

CN201710630418.4 discloses a meso- and macroporous silica-alumina material and its preparation. The meso- and macroporous silica-alumina material has an anhydrous chemical composition of (0-0.3) Na$_2$O:(2-18) Al$_2$O$_3$:(82-98) SiO$_2$, calculated by weight of oxides; a pore volume of 0.8-2 mL/g, a specific surface area of 150-350 m$^2$/g, a most probable pore diameter of 30-100 nm, and a B/L acid ratio of 0.8-2.0. The silica-alumina material has the characteristics of high pore volume, large pore diameter and high B/L acid ratio, and meanwhile, the preparation method employs a cheap silica-alumina source, does not need the use of an organic template, and has the characteristics of low cost and simple operation. The ammonium salt exchange involved in the method is performed by subjecting the solid precipitate obtained by filtration to exchange at a weight ratio of the precipitate (on a dry basis): ammonium salt: H$_2$O=1:(0.1-1):(5-10) at a temperature of from room temperature to 100° C. for 1-3 times, each time for 0.3-1 hour, until the content by mass of sodium in the solid precipitate is lower than 0.3 wt %. The ammonium salt used for exchange is one or more selected from ammonium chloride, ammonium nitrate, ammonium carbonate, ammonium sulfate and ammonium bicarbonate.

CN201710102634.1 discloses a silica-alumina material, its preparation and application thereof. The silica-alumina material has a chemical composition of (0-0.3) Na$_2$O·(50-80) SiO$_2$·(20-50)Al$_2$O$_3$, calculated by weight of oxides as measured by XRF, wherein the silica-alumina material has an XRD pattern showing only a diffuse diffraction peak at 25°-27°, a most probable pore diameter of 20-50 nm, and x/y=0.55-0.75, wherein x represents the Si/Al atomic ratio measured by the XPS method, and y represents the Si/Al atomic ratio measured by the XRF method.

DISCLOSURE OF THE INVENTION

The inventors of the present application have found that the difficulty in preparing macroporous silica-alumina materials is that, with the increase of silica content, the pore volume of the silica-alumina material is gradually reduced, while the sodium content is remarkably increased, and thus how to effectively reduce the sodium content while providing a large pore volume is very critical. However, in existing methods for producing silica-alumina materials, in order to reduce the impurity content of the silica-alumina material, especially the sodium content, ion exchange with ammonium salt is performed, which makes the treatment process complicated, and increases the production cost of the silica-alumina material. The inventors of the present application have also found that silica sol with higher price is typically used as a silicon source in industry to reduce the times of subsequent sodium removal by washing, or ion exchange is employed to realize sodium removal, but these sodium removal methods greatly increase the production cost of the silica-alumina material, and have poor economical efficiency, which limits the large-scale industrial popularization and application of them. Therefore, the inventors of the present application believe that preparing a macroporous silica-alumina material while reducing the cost for removing sodium is an effective way to prepare a silica-alumina material with excellent performance and low price. Then, after assiduous studying, the inventors of the present application have found a novel silica-alumina material. The present application has been completed based on this finding.

Particularly, the present application relates to the following aspects.

1. A silica-alumina material, having a SiO$_2$/Al$_2$O$_3$ molar ratio of from 0.8 to 1.5 (preferably from 1.0 to 1.4), comprising a lamellar structure having an average length of from 0.5 to 2 μm (preferably from 0.5 to 1.5 μm) and an average thickness of from 30 to 80 nm (preferably from 30 to 75 nm), which in calcined form has an XRD pattern substantially as shown in Table I or Table II below, preferably has an XRD pattern substantially as shown in FIG. 2,

TABLE I

| 2θ | d-spacing (nm) | Relative strength |
|---|---|---|
| 14.0 | 0.12-0.13 | VS |
| 24.3 | 0.18-0.19 | VS |
| 34.3 | 0.07-0.08 | S |
| 42.6 | 0.11-0.13 | M |
| 51.9 | 0.10-0.13 | M |
| 66.4 | 0.06-0.08 | M |

TABLE II

| 2θ | d-spacing (nm) | Relative strength |
|---|---|---|
| 13.9 | 0.12-0.13 | VS |
| 24.2 | 0.17-0.18 | VS |
| 31 | 0.36-0.38 | M |
| 34.4 | 0.08-0.10 | S |
| 39.9 | 0.08-0.10 | M |
| 42.5 | 0.11-0.12 | M |
| 51.6 | 0.12-0.13 | W |
| 57.8 | 0.14-0.16 | W |
| 66.4 | 0.07-0.09 | W | where the intensity value of the strongest diffraction peak in the XRD pattern is set to 100, W means weak, i.e. relative intensity>0 to ≤20, M means medium, i.e. relative intensity>20 to ≤40, S means strong, i.e. relative intensity>40 to ≤60, and VS means very strong, i.e. relative intensity>60 to ≤100.

2. The silica-alumina material according to any one of the preceding aspects, having a pore volume of not less than 1.1 mL/g (preferably more than 1.15 mL/g, and more preferably 1.15-1.5 mL/g), and/or a specific surface area of 260-340 m²/g (preferably 260-310 m²/g), and/or a pore distribution as follows: the pore volume of pores with a pore diameter of <10 nm accounts for ≤5% of the total pore volume (preferably the pore volume of pores with a pore diameter of <10 nm accounts for 3% of the total pore volume) and the pore volume of pores with a pore diameter of 10-50 nm accounts for 65-85% of the total pore volume (preferably the pore volume of pores with a pore diameter of 10-50 nm accounts for 70-85% of the total pore volume), the pore volume of pores with a pore diameter of >50 nm accounts for 10-30% of the total pore volume (preferably the pore volume of pores with a pore diameter of >50 nm accounts for 12-25% of the total pore volume) and/or an average pore diameter of 14-23 nm (preferably 16-21 nm).

3. A silica-alumina material according to any one of the preceding aspects, having a B acid content of greater than 0.08 mmol/g (preferably 0.1 to 0.2 mmol/g or 0.1 to 0.15 mmol/g) and/or a ratio of B acid to L acid of 0.2 to 0.8 (preferably 0.3 to 0.7) and/or a $Na_2O$ content of less than 0.3 wt % (preferably less than 0.2 wt %) and/or an absorption peak at a chemical shift of −87 ppm to −89 ppm in its Si-NMR spectrum and an absorption peak at a chemical shift of around 57 ppm in its Al-NMR spectrum and/or showing no diffraction peak, when present in a calcined form, in its small-angle XRD pattern.

4. The silica-alumina material according to any one of the preceding aspects, further comprising a non-lamellar structure, wherein the lamellar structure accounts for 3% or more (preferably 5% or more, more preferably 10-80% or 10-60%) of the total volume of the silica-alumina material.

5. A method for producing a silica-alumina material, comprising the following steps sequentially:

(1) adding an acidic aluminum source into a silicon source to obtain a mixture A,
(2) contacting said mixture A with an alkaline aluminum source in the presence of water to obtain a slurry B, and
(3) subjecting the slurry B to a hydrothermal treatment to obtain the silica-alumina material.

6. The method according to any one of the preceding aspects, wherein in step (1), the silicon source is a water-soluble or water-dispersible alkaline silicon-containing compound (preferably a water-soluble or water-dispersible alkaline inorganic silicon-containing compound, more preferably one or more selected from water-soluble silicates, silicate sodium and silica sol, preferably silicate sodium), and/or the silicon source is used in the form of an aqueous solution, and the concentration of the silicon source (calculated as $SiO_2$) is 5 to 30 wt % (preferably 15 to 30 wt %), based on the total weight of the aqueous solution, and/or the acidic aluminum source is a water-soluble acidic aluminum-containing compound (preferably a water-soluble acidic inorganic aluminum-containing compound, particularly a water-soluble inorganic aluminum salt of a strong acid, more preferably one or more selected from aluminum sulfate, aluminum nitrate, and aluminum chloride, preferably aluminum sulfate), and/or the acidic aluminum source is used in the form of an aqueous solution, and the concentration of the acidic aluminum source (calculated as $Al_2O_3$) is 30-100 g/L (preferably 30-80 g/L), based on the total weight of the aqueous solution, and/or the weight ratio of the silicon source (calculated as $SiO_2$) to the acidic aluminum source (calculated as $Al_2O_3$) is 1:1 to 9:1 (preferably 1:1 to 7:1).

7. The method according to any one of the preceding aspects, wherein in step (1), an acid is further added (preferably, the acidic aluminum source is added to the silicon source, and then the acid is added to obtain the mixture A), and/or the acid is a water-soluble acid (preferably, a water-soluble inorganic acid, more preferably, one or more selected from sulfuric acid, nitric acid, and hydrochloric acid, and preferably, sulfuric acid), and/or the acid is used in the form of an aqueous solution, and the concentration of the acid is 2 to 6 wt % (preferably, 2 to 5 wt %), based on the total weight of the aqueous solution, and/or the acid is added in such an amount that the pH of the mixture A is 2 to 4 (preferably, 3 to 4).

8. The method according to any one of the preceding aspects, wherein in step (2), the alkaline aluminum source is a water-soluble alkaline aluminum-containing compound (preferably a water-soluble alkaline inorganic aluminum-containing compound, especially a metaaluminate of an alkali metal, more preferably one or more selected from sodium metaaluminate and potassium metaaluminate, preferably sodium metaaluminate), and/or the alkaline aluminum source is used in the form of an aqueous solution, and the concentration of the alkaline aluminum source (calculated as $Al_2O_3$) is 130-350 g/L (preferably 150-250 g/L), based on the total weight of the aqueous solution, and/or based on the total volume of the mixture A, the alkaline aluminum source and water, the amount of the mixture A used is 40-80 vol % (preferably 45-75 vol %), and/or based on the total volume of the mixture A, the alkaline aluminum source and water, the amount of the alkaline aluminum source used is 10 to 30 vol % (preferably 12 to 25 vol %), and/or based on the total volume of the mixture A, the alkaline aluminum source and water, the amount of water used is 10 to 30 vol % (preferably 10 to 25 vol %), and/or the mixture A and the alkaline aluminum source are added to the water sequentially or simultaneously (preferably mixture A and the alkaline aluminum source are added to the water concurrently), and/or the mixture A is added at a flow rate of 15 to 50 mL/min (preferably 20 to 40 mL/min), and/or the alkaline aluminum source is added at a flow rate that is controlled to maintain the pH value of the slurry B at 7.5 to 10.5 (preferably 8.0 to 10.5, and further preferably 8.5 to 10.5).

9. The method according to any one of the preceding aspects, wherein in step (2), a water-soluble carbonate is further added (preferably, the mixture A and the alkaline aluminum source are added to water, and then the water-soluble carbonate is added to obtain the slurry B), and/or the water-soluble carbonate is selected from carbonates of one or more of alkali metals and ammonium (preferably, one or more selected from sodium carbonate, potassium carbonate, sodium bicarbonate, potassium bicarbonate, ammonium carbonate, ammonium bicarbonate, preferably sodium carbonate), and/or the water-soluble carbonate is used in a solid form, and/or the water-soluble carbonate is added in such an amount that the pH of the slurry B is 10.5 to 12 (preferably, 11 to 12).

10. The method according to any one of the preceding aspects, wherein in step (3), the silica-alumina material is separated (such as by filtration or centrifugation) from the reaction system of the hydrothermal treatment, washed till neutral, and then dried, and/or the drying conditions include: a drying temperature of 100-150° C., and a drying time of 6-10 hours.

11. The method according to any one of the preceding aspects, wherein in step (1), the temperature is from 25° C. to 50° C. (preferably from 25° C. to 40° C.), the pressure is normal pressure, and/or, in step (2), the temperature is from 50° C. to 90° C. (preferably from 50° C. to 80° C.), the pressure is normal pressure, and/or, in step (3), the temperature is from 180° C. to 300° C. (preferably from 180° C. to 280° C., further preferably from 180° C. to 250° C.), the pressure is from 0.1 MPa to 0.5 MPa (preferably from 0.1 MPa to 0.3 MPa), and/or, in step (3), where the initial time of the hydrothermal treatment is set to $t_0$, the time at which the reaction system of the hydrothermal treatment reaches the highest viscosity is set to $t_{max}$, and $\Delta t = t_{max} - t_0$, the time (expressed in unit h) of the hydrothermal treatment is from $\Delta t + 1$ to $\Delta t + 20$ (preferably from $\Delta t + 2$ to $\Delta t + 12$, particularly from $\Delta t + 4$ to $\Delta t + 8$), and/or, in step (3), the hydrothermal treatment is carried out for a period of time ranging from 6 to 20 h (preferably from 8 to 12 h).

12. The method according to any one of the preceding aspects, wherein an auxiliary agent (preferably one or more selected from phosphorus, boron and titanium) is further added, and/or the auxiliary agent is used in an amount of 1-8 wt % (preferably 2-6 wt %), calculated as oxide and relative to 100 wt % of the total weight of the silica-alumina material.

13. A catalytic material, comprising an active metal component and a silica-alumina material according to any one of the preceding aspects or a silica-alumina material produced by a method according to any one of the preceding aspects.

14. The catalytic material according to any one of the preceding aspects, wherein the active metal component is a metal component having hydrogenation activity (preferably at least one selected from the group consisting of Group VIB metals and Group VIII metals of the periodic table, particularly at least one selected from Mo, W, Ni and Co), and/or the active metal component is present in an amount of 5-30 wt % (preferably 5-25 wt %), calculated as oxide and based on the total weight of the catalytic material.

15. A hydrogenation process, comprising a step of subjecting a hydrocarbon-containing material to a hydrogenation reaction in the presence of the catalytic material according to any one of the preceding aspects.

16. The process according to any one of the preceding aspects, wherein the hydrocarbon-containing material is at least one selected from diesel oil, Vacuum gas oil, heavy oil, coal tar, ethylene tar, and catalytic slurry oil, and/or the conditions of the hydrogenation reaction include: a reaction pressure of 5-20 MPaG, a reaction temperature of 300-450° C., a liquid hourly space velocity of 0.1-1.5 h$^{-1}$, and a hydrogen-to-oil volume ratio of 100-1000.

Technical Effects (1) The silica-alumina material of the present application has the characteristics of large pore volume, and two-stage gradient pore channels of mesopores and macropores, as well as high B acid content as in molecular sieve, and due to the occurrence of the lamellar structure, the silica-alumina material begins to show crystal characteristics of a molecular sieve, and has low impurity content (especially low sodium content), and thus is suitable for use as a carrier for catalytic materials, and is particularly suitable for use as a carrier for heavy oil hydrogenation catalysts.

(2) In the method for producing the silica-alumina material according to the present application, a silicon source is contacted with an acidic aluminum source, particularly, the silicon source is further contacted with an acid in preferred embodiments, cations (sodium ions and the like) in silicic acid polymers enveloped in a ring or a cage in the silicon source are dissociated, acidified silica micelle is adsorbed on aluminum hydroxide colloid, so that sodium ions are effectively separated from the silica micelle, the acidic aluminum source added plays a role in isolating the dissociated cations, and therefore the cations (sodium ions) are easier to remove, the difficulty in removing sodium by subsequent washing is greatly reduced, and the water consumption for washing can be reduced. More importantly, cations (sodium ions) can be effectively removed, and the acid sites occupied by Na can be recovered, so that the silica-alumina material has higher acidity.

(3) In the method for producing the silica-alumina material of the present application, the acidified silica micelle is adsorbed on the aluminum hydroxide colloid, so that a crystal nucleus is provided for subsequent reaction, the enlargement of the crystal grain of the silica-alumina material produced is promoted, and a silica-alumina material with large pore volume and large pore diameter is favorably formed.

(4) In the method for producing the silica-alumina material of the present application, in preferred embodiments, the pH value of the slurry B is adjusted by adding a water-soluble carbonate, then, in the treatment process under certain temperature and certain pressure, the slurry system is changed from an initial flowing state into a thixotropic form similar to a gel, during which the viscosity of the reaction system is gradually increased and reaches a peak value, then the slurry system is changed back into the flowing state after being treated for a period of time, during which the viscosity of the reaction system is gradually reduced, and in the process of changing into the thixotropic form similar to a gel, the silica-alumina material and water mutually form a variable structure of silicon-aluminum-oxygen network, so that a silica-alumina material with large pore volume is favorably produced.

(5) By adjusting the SiO$_2$/Al$_2$O$_3$ ratio and using high temperature hydrothermal conditions, the carbonate added promotes the oriented growth of the lamellar structure of the silica-alumina crystal grains, and the content of the lamellar structure increases with the increase of the treatment time. The generation of the lamellar structure changes the bonding form between Si and Al, and promotes the increase of the content of B acid.

BRIEF DESCRIPTION OF THE DRAWINGS

FIG. 1 shows an SEM image of the silica-alumina material obtained in Example 1 of the present application.

FIG. 2 shows an XRD pattern of the silica-alumina material obtained in Example 1 of the present application (as the time of the hydrothermal treatment, h1=8 hours, h2=16 hours).

FIG. 3 shows a Si-NMR spectrum of the silica-alumina material obtained in Example 1 of the present application (as the time of the hydrothermal treatment, h1=8 hours, h2=16 hours).

FIG. 4 shows an Al-NMR spectrum of the silica-alumina material obtained in Example 1 of the present application (as the time of the hydrothermal treatment, h1=8 hours, h2=16 hours).

DETAILED DESCRIPTION OF THE INVENTION

Figure 5:
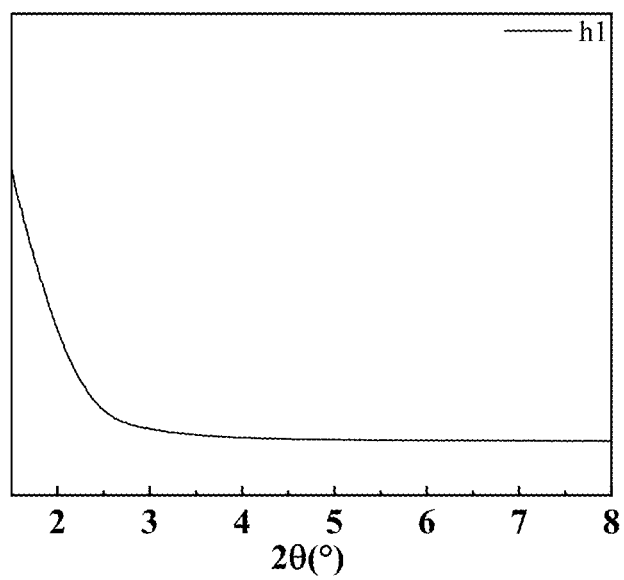
FIG. 5 shows a small-angle XRD pattern of the silica-alumina material obtained in Example 1 of the present application.

The present application will be illustrated in detail hereinbelow with reference to embodiments thereof, but it should be noted that the scope of the present application is not limited by those embodiments, but is defined by the appended claims.

All publications, patent applications, patents, and other references cited herein are incorporated by reference in their entirety. Unless defined otherwise, all technical and scientific terms used herein have the same meaning as commonly understood by those skilled in the art. In case of conflict, the contents described herein, including definitions, should prevail.

Where a material, substance, method, step, device, component, or the like is described herein as "commonly known to those skilled in the art", "prior art" or the like, it is to be understood that said material, substance, method, step, device and component cover not only those conventionally used in the art at the time of filing the present application, but also those not commonly used at present but will become commonly known in the art to be suitable for a similar purpose.

In the context of the present application, unless explicitly stated to the contrary, both the silica-alumina material and the catalyst are subjected to a calcination treatment, sometimes referred to as "calcined form", prior to the measurement being made. Here, the conditions of the calcination treatment include: air atmosphere, a calcining temperature of 600° C., and a calcining time of 3 h or more.

In the context of the present application, the pore volume, specific surface area, average pore diameter and pore distribution of silica-alumina materials and catalysts are measured using low temperature nitrogen adsorption method.

In the context of the present application, the total acid, the B acid and the L acid of silica-alumina materials and catalysts are measured using pyridine infrared adsorption method.

In the context of the present application, the contents of sodium oxide, alumina and silica of silica-alumina materials are measured using fluorescence analysis.

In the context of the present application, the active metal content of catalysts is measured using spectrophotometric method.

In the context of the present application, the abrasion index is measured using air-jet method.

In the context of the present application, the X-ray diffraction (XRD) characterization is conducted using a D/max2500 X-ray diffraction analyzer manufactured by RIGAKU, Japan, at an operating voltage of 40 kV, an operating current of 40 mA, a scan range of 10 (°) to 70(°), a step size of 0.06(°), and a scan rate of 0.21 (°) min$^{-1}$.

In the context of the present application, the small-angle XRD characterization is conducted using a D/max2500 X-ray diffraction analyzer, manufactured by RIGAKU, Japan, at an operating voltage of 40 k, an operating current of 40 mA, a scan range of 1.5(°) to 8(°), a step size of 0.01 (°), and a scan rate of 0.02 (°) min$^{-1}$.

In the context of the present application, the sample morphology characterization (SEM) is conducted using a JXM-7500F Field Emission Scanning Electron Microscope, manufactured by JEOL, at an operating voltage of 6.5 eV, an accelerating voltage of 5.0 kV, and a magnification factor of thirty thousand times.

In the context of the present application, the solid-state nuclear magnetic resonance $^{27}$Al MAS NMR experiment is conducted on a Bruker-Avance III-400 solid-state NMR spectrometer, on which the resonance frequencies of the $^{1}$H and $^{27}$Al nuclei are 399.33 and 104.05 MHz, respectively. The $^{27}$Al MAS NMR is acquired on a 4 mm dual resonance probe using a single-pulse platelet corner (<π/12, 0.21 μs) technique with a pulse delay time of 1 s. The chemical shift of $^{27}$Al spectrum is calibrated with 1M Al(NO$_3$)$_3$.

In the context of the present application, solid-state nuclear magnetic resonance $^{29}$Si MAS NMR experiment is conducted on a Varian Infinity plus-600 solid-state NMR spectrometer, on which the resonance frequencies of the $^{1}$H and $^{29}$Si nuclei are 599.51 and 120.35 MHz, respectively. $^{29}$Si MAS NMR is acquired on a 7.5 mm dual-resonance probe using a single-pulse high-power decoupling technique with a π/2 pulse width of 6.1 μs, a pulse delay time of 80 s, and a rotation speed of 5 kHz. The chemical shift of the $^{29}$Si spectrum is calibrated with kaolin (−91.5 ppm).

In the context of the present application, the average particle size of silica-alumina materials is obtained by taking statistics on 20 different SEM images with a magnification factor of thirty thousand times and then taking an average.

In the context of the present application, the average particle size of primary particles of silica-alumina materials is obtained by taking statistics on 20 different SEM images with a magnification factor of thirty thousand times and then taking an average.

In the context of the present application, the average length and average thickness of the lamellar structure are obtained by taking statistics on 20 different SEM images with a magnification factor of thirty thousand times and then taking an average.

In the context of the present application, the viscosity of the reaction system may be measured by any method, as long as an effective comparison can be made with the increase of the reaction time, and there is no particular limitation here.

In the context of the present application, unless specifically stated otherwise, all percentages, parts, ratios, etc. are expressed by weight and all pressures given are gauge pressures.

In the context of the present application, any two or more embodiments of the present application may be arbitrarily combined, and the resulting technical solution forms a part of the initial disclosure of the present application and falls within the scope of the present application.

According to an embodiment of the present application, it relates to a silica-alumina material having a $SiO_2/Al_2O_3$ molar ratio of 0.8-1.5 (preferably 1.0-1.4).

According to an embodiment of the present application, the silica-alumina material comprises a lamellar structure having an average length of 0.5-2 μm (preferably 0.5-1.5 μm) and an average thickness of 30-80 nm (preferably 30-75 nm). This can be confirmed by SEM image.

According to an embodiment of the present application, the calcined form of the silica-alumina material has an XRD pattern substantially as shown in Table I below.

TABLE I

| 2θ | d-spacing (nm) | Relative strength |
|---|---|---|
| 14.0 | 0.12-0.13 | VS |
| 24.3 | 0.18-0.19 | VS |
| 34.3 | 0.07-0.08 | S |
| 42.6 | 0.11-0.13 | M |
| 51.9 | 0.10-0.13 | M |
| 66.4 | 0.06-0.08 | M |

TABLE I (preferred)

| 2θ | d-spacing (nm) | Relative strength |
|---|---|---|
| 14.0 | 0.117 | VS |
| 24.3 | 0.190 | VS |
| 34.3 | 0.078 | S |
| 42.6 | 0.121 | M |
| 51.9 | 0.106 | M |
| 66.4 | 0.079 | M |

According to an embodiment of the present application, the calcined form of the silica-alumina material preferably has an XRD pattern substantially as shown in Table II below.

TABLE II

| 2θ | d-spacing (nm) | Relative strength |
|---|---|---|
| 13.9 | 0.12-0.13 | VS |
| 24.2 | 0.17-0.18 | VS |
| 31 | 0.36-0.38 | M |
| 34.4 | 0.08-0.10 | S |
| 39.9 | 0.08-0.10 | M |
| 42.5 | 0.11-0.12 | M |
| 51.6 | 0.12-0.13 | W |
| 57.8 | 0.14-0.16 | W |
| 66.4 | 0.07-0.09 | W |

TABLE II (preferred)

| 2θ | d-spacing (nm) | Relative strength |
|---|---|---|
| 13.9 | 0.125 | VS |
| 24.2 | 0.171 | VS |
| 31 | 0.373 | M |
| 34.4 | 0.077 | S |
| 39.9 | 0.086 | M |
| 42.5 | 0.114 | M |
| 51.6 | 0.124 | W |
| 57.8 | 0.142 | W |
| 66.4 | 0.079 | W |

According to the present application, where the intensity value of the strongest diffraction peak in the XRD pattern is set to 100, W means weak, i.e. relative intensity>0 to ≤20, M means medium, i.e. relative intensity>20 to ≤40, S means strong, i.e. relative intensity>40 to ≤60, and VS means very strong, i.e. relative intensity>60 to ≤100.

According to an embodiment of the present application, the calcined form of the silica-alumina material has an XRD pattern substantially as shown in FIG. 2.

According to an embodiment of the present application, the silica-alumina material has a pore volume of not less than 1.1 mL/g (preferably more than 1.15 mL/g, and more preferably 1.15 to 1.5 mL/g).

According to an embodiment of the present application, the silica-alumina material has a specific surface area of 260-340 m²/g (preferably 260-310 m²/g).

According to an embodiment of the present application, the silica-alumina material has a pore distribution as follows: the pore volume of pores with a pore diameter of <10 nm accounts for ≤5% of the total pore volume (preferably, the pore volume of pores with a pore diameter of <10 nm accounts for 3% of the total pore volume), the pore volume of pores with a pore diameter of 10-50 nm accounts for 65%-85% of the total pore volume (preferably, the pore volume of pores with a pore diameter of 10-50 nm accounts for 70%-85% of the total pore volume) and the pore volume of pores with a pore diameter of >50 nm accounts for 10%-30% of the total pore volume (preferably, the pore volume of pores with a pore diameter of >50 nm accounts for 12%-25% of the total pore volume).

According to an embodiment of the present application, the silica-alumina material has an average pore size of 14 to 23 nm (preferably 16 to 21 nm).

According to an embodiment of the present application, the silica-alumina material has a B acid content of more than 0.08 mmol/g (preferably 0.1 to 0.2 mmol/g or 0.1 to 0.15 mmol/g).

According to an embodiment of the present application, the silica-alumina material has a ratio of B acid to L acid of 0.2 to 0.8 (preferably 0.3 to 0.7).

According to an embodiment of the present application, the silica-alumina material has a $Na_2O$ content of less than 0.3 wt % (preferably less than 0.2 wt %).

According to an embodiment of the present application, the silica-alumina material has an average particle size of 30 to 100 nm (preferably 30 to 80 nm).

According to an embodiment of the present application, the silica-alumina material has an absorption peak at a chemical shift of −87 ppm to −89 ppm in its Si-NMR spectrum, indicating that a silicon-oxygen tetrahedron is directly connected with three aluminum-oxygen tetrahedrons.

According to an embodiment of the present application, the silica-alumina material has an absorption peak around a chemical shift of 57 ppm in its Al-NMR spectrum, indicating the presence of tetracoordinated framework aluminum in the material.

According to an embodiment of the present application, the calcined form of the silica-alumina material has no diffraction peak in its small-angle XRD pattern, indicating the absence of characteristic peaks of molecular sieve.

According to an embodiment of the present application, the silica-alumina material further comprises a non-lamellar structure. This can be confirmed by SEM image. Here, the non-lamellar structure is an aggregate of a plurality of primary aluminosilicate particles, showing the characteristics of amorphous aluminosilicate. In addition, the primary aluminosilicate particles typically have an average particle size of 5 to 25 nm (preferably 10 to 25 nm).

According to an embodiment of the present application, the lamellar structure accounts for 3% or more (preferably 5% or more, more preferably 10% to 80% or 10% to 60%) of the total volume of the silica-alumina material.

According to an embodiment of the present application, it also relates to a method for producing a silica-alumina material, and the method can be used for producing the silica-alumina material described hereinabove.

According to an embodiment of the present application, the method comprises the following steps in sequence:
(1) adding an acidic aluminum source into a silicon source to obtain a mixture A,
(2) contacting said mixture A with an alkaline aluminum source in the presence of water to obtain a slurry B, and
(3) subjecting the slurry B to a hydrothermal treatment to obtain the silica-alumina material.

According to the present application, in step (1), the acidic aluminum source is added to the silicon source, rather than adding the silicon source into the acidic aluminum source, which would otherwise result in the formation of a large amount of precipitate.

According to an embodiment of the present application, in step (1) of the method, the silicon source is a water-soluble or water-dispersible alkaline silicon-containing compound (preferably a water-soluble or water-dispersible alkaline inorganic silicon-containing compound, more preferably one or more selected from the group consisting of water-soluble silicate, water glass, and silica sol, and preferably water glass).

According to an embodiment of the present application, in the method, the silicon source is used in the form of an aqueous solution. The concentration of the silicon source (calculated as $SiO_2$) is 5-30 wt % (preferably 15-30 wt %), based on the total weight of the aqueous solution, and a modulus typically of 2.5 to 3.2.

According to an embodiment of the present application, in the method, the acidic aluminum source is a water-soluble acidic aluminum-containing compound (preferably a water-soluble acidic inorganic aluminum-containing compound, particularly a water-soluble inorganic aluminum salt of a strong acid, more preferably one or more selected from aluminum sulfate, aluminum nitrate, and aluminum chloride, and preferably aluminum sulfate).

According to an embodiment of the present application, in the method, the acidic aluminum source is used in the form of an aqueous solution, and the concentration of the acidic aluminum source (calculated as $Al_2O_3$) is 30 to 100 g/L (preferably 30 to 80 g/L), based on the total weight of the aqueous solution.

According to an embodiment of the present application, in the method, a weight ratio of the silicon source (calculated as $SiO_2$) to the acidic aluminum source (calculated as $Al_2O_3$) is 1:1 to 9:1 (preferably 1:1 to 7:1).

According to an embodiment of the present application, in the method, to achieve a more excellent technical effect in the present application, particularly, to obtain a silica-alumina material with a larger pore volume and a lower impurity content, in step (1), an acid is further added (preferably, the acidic aluminum source is added to the silicon source, and then the acid is added to obtain the mixture A).

According to an embodiment of the present application, in the method, the acid is a water-soluble acid (preferably a water-soluble inorganic acid, more preferably one or more selected from sulfuric acid, nitric acid, and hydrochloric acid, and preferably sulfuric acid).

According to an embodiment of the present application, in the method, the acid is used in the form of an aqueous solution. The acid has a concentration of 2-6 wt % (preferably 2-5 wt %), based on the total weight of the aqueous solution.

According to an embodiment of the present application, in the method, the acid is added in such an amount that the pH of the mixture A is 2 to 4 (preferably 3 to 4).

According to an embodiment of the present application, in step (1) of the method, typically, the mixture A has an aluminum content of 5 to 20 g $Al_2O_3$/L (calculated as $Al_2O_3$) and a silicon content of 5 to 40 g $SiO_2$/L (calculated as $SiO_2$).

According to an embodiment of the present application, in step (2) of the method, the alkaline aluminum source is a water-soluble alkaline aluminum-containing compound (preferably a water-soluble alkaline inorganic aluminum-containing compound, particularly a metaaluminate of an alkali metal, more preferably one or more selected from sodium metaaluminate and potassium metaaluminate, preferably sodium metaaluminate).

According to an embodiment of the present application, in the method, the alkaline aluminum source is used in the form of an aqueous solution. The concentration of the alkaline aluminum source (calculated as $Al_2O_3$) is 130-350 g/L (preferably 150-250 g/L), based on the total weight of the aqueous solution, and its caustic ratio is typically 1.15-1.35, preferably 1.15-1.30.

According to an embodiment of the present application, in the method, the mixture A is used in an amount of 40 to 80 vol % (preferably 45 to 75 vol %), based on the total volume of the mixture A, the alkaline aluminum source, and water.

According to an embodiment of the present application, in the method, the alkaline aluminum source is used in an amount of 10 to 30 vol % (preferably 12 to 25 vol %), based on the total volume of the mixture A, the alkaline aluminum source and water.

According to an embodiment of the present application, in the method, the water is used in an amount of 10 to 30 vol % (preferably 10 to 25 vol %), based on the total volume of the mixture A, the alkaline aluminum source, and water.

According to an embodiment of the present application, in the method, the mixture A and the alkaline aluminum source are added to water sequentially or simultaneously (preferably, the mixture A and the alkaline aluminum source are added to water concurrently).

According to an embodiment of the present application, in the method, the mixture A is added at a flow rate of 15 to 50 mL/min (preferably 20 to 40 mL/min).

According to an embodiment of the present application, in the method, the alkaline aluminum source is added at a flow rate that is controlled to maintain the pH of the slurry B at 7.5 to 10.5 (preferably 8.0 to 10.5, and more preferably 8.5 to 10.5).

According to an embodiment of the present application, in the method, to achieve a more excellent technical effect in the present application, particularly to obtain a silica-alumina material with a larger pore volume, in step (2), a water-soluble carbonate is further added (preferably, the mixture A and the alkaline aluminum source are added to water, and then the water-soluble carbonate is further added to obtain the slurry B).

According to an embodiment of the present application, in the method, the water-soluble carbonate is selected from carbonates of one or more of alkali metals and ammonium (preferably, one or more of sodium carbonate, potassium carbonate, sodium bicarbonate, potassium bicarbonate, ammonium carbonate, and ammonium bicarbonate, and preferably sodium carbonate).

According to an embodiment of the present application, in the method, the water-soluble carbonate is used in the form of a solid.

According to an embodiment of the present application, in the method, the water-soluble carbonate is added in such an amount that the pH of the slurry B is 10.5 to 12 (preferably 11 to 12).

According to an embodiment of the present application, in the method, in step (3), the silica-alumina material is separated from the reaction system of the hydrothermal treatment, washed till neutral, and then dried. Here, the washing may be performed by a washing method conventionally used in the art, preferably by washing with deionized water, and more preferably at 50° C. to 90° C.

In addition, the separation can be performed by any means in the art useful for carrying out the separation of liquid-solid two-phase materials, such as filtration, centrifugal separation and the like, and particularly, the separation can be performed by filtration to obtain a solid material and a liquid material after the separation, and the solid material is washed and dried to obtain the silica-alumina material.

According to an embodiment of the present application, in the method, the conditions of the drying include: a drying temperature of 100-150° C., and a drying time of 6-10 hours.

According to an embodiment of the present application, in step (1) of the method, the temperature is 25 to 50° C. (preferably 25 to 40° C.), and the pressure is normal pressure.

According to an embodiment of the present application, in step (2) of the method, the temperature is 50 to 90° C. (preferably 50 to 80° C.), and the pressure is normal pressure.

According to an embodiment of the present application, in step (3) of the method, the temperature is 180-300° C. (preferably 180-280° C., further preferably 180-250° C.) and the pressure is 0.1-0.5 MPa (preferably 0.1-0.3 MPa).

According to an embodiment of the present application, in the method, to achieve a more excellent technical effect in the present application, particularly, to obtain a higher proportion of the lamellar structure, in step (3), where the initial time of the hydrothermal treatment is set to $t_0$, the time at which the reaction system of the hydrothermal treatment reaches the highest viscosity is set to $t_{max}$, and $\Delta t = t_{max} - t_0$, the time (expressed in unit h) of the hydrothermal treatment is from $\Delta t+1$ to $\Delta t+20$ (preferably from $\Delta t+2$ to $\Delta t+12$, particularly from $\Delta t+4$ to $\Delta t+8$). Alternatively, in step (3), the time of the hydrothermal treatment may be 6 to 20 hours (preferably 8 to 12 hours), from the viewpoint of easy control of the method.

According to an embodiment of the present application, in the method, one or more additive agents, such as $P_2O_5$, $B_2O_3$ or $TiO_2$, can be added according to actual needs. For this purpose, these precursors may be added in the form of water-soluble inorganic salts during the reaction of step (1). Specific examples of the inorganic salts include borates, sulfates, and nitrates. Furthermore, the amounts of these auxiliary agents added may be arbitrarily adjusted according to the requirements of subsequent processes, such as the catalyst and the like. In general, these auxiliary agents are typically added in an amount, calculated as oxide, of from 1% to 8% by weight, preferably from 2% to 6% by weight, relative to 100% by weight of the total weight of the silica-alumina material.

According to an embodiment of the present application, it also relates to a catalytic material, comprising an active metal component and the silica-alumina material according to the present application or the silica-alumina material produced by the method according to the present application.

According to an embodiment of the present application, the active metal component is a metal component having hydrogenation activity (preferably at least one selected from metals of Groups VIB and VIII of the periodic table, particularly at least one selected from Mo, W, Ni and Co).

According to an embodiment of the present application, the active metal component (calculated as oxide) is present in an amount of 5-30 wt % (preferably 5-25 wt %), based on the total weight of the catalytic material.

According to an embodiment of the present application, it also relates to a hydrogenation process, comprising a step of subjecting a hydrocarbon-containing material to a hydrogenation reaction in the presence of the catalytic material as previously described in the present application.

According to an embodiment of the present application, the hydrocarbon-containing material is at least one selected from diesel oil, vacuum gas oil, heavy oil, coal tar, ethylene tar, and catalytic slurry oil.

According to an embodiment of the present application, the conditions of the hydrogenation reaction include: a reaction pressure of 5-20 MPaG, a reaction temperature of 300-450° C., a liquid hourly space velocity of 0.1-1.5 $h^{-1}$, and a hydrogen-to-oil volume ratio of 100-1000.

EXAMPLES

The present application will be further illustrated in detail with reference to the following examples, but the present application is not limited to those examples.

In the following examples and comparative examples, all of the reagents and raw materials are either commercially available or can be prepared according to prior knowledge.

Example 1

(1) Production of Silica-Alumina Material

An aluminum sulfate solution with a concentration of 50 g $Al_2O_3$/L and a silica sol solution with a concentration of 50 g $SiO_2$/L and a modulus of 2.8 were prepared for further use, and a dilute sulfuric acid solution with a concentration of 1 mol/L was prepared for further use. A sodium metaaluminate solution with a causticity ratio of 1.25 and a concentration of 160 g $Al_2O_3$/L was prepared for further use.

1.44 L of the silica sol solution with a concentration of 50 g $SiO_2$/L was measured and added into a container, and 1 L of the aluminum sulfate solution with a concentration of 50 g $Al_2O_3$/L was slowly added under stirring, during which process aluminum hydroxide colloid was generated, but the solution was still present as a liquid. Then, the 1 mol/L dilute sulfuric acid solution was added, the pH value was adjusted to 3.5, and an acidification treatment was performed to obtain a mixed liquor A.

700 mL of deionized water was added as bottom water into a 5000 mL reactor, stirring and heating were started, the deionized water was heated to 80° C., the mixed liquor A was added into the reactor at a rate of 28 mL/min, the prepared sodium metaaluminate solution was added concurrently at the same time, the pH value of the reaction was controlled to 8.3 by adjusting the flow rate of the sodium metaaluminate solution, and the temperature and the pH value of the slurry in the reactor were kept constant. After the reaction was completed, the amount of sodium metaaluminate added was 325 mL, and 75 g of ammonium carbonate was added into the reactor under stirring to adjust the pH value to 10.8. The slurry was charged into a reactor and treated for 8 hours (corresponding to Δt+6 hours) with stirring at a treatment temperature of 210° C. and a treatment pressure of 0.4 MPa. The treated slurry was washed with hot water at 90° C. until the liquid was neutral, dried at 120° C. for 6 h to obtain a dry sample PO-1, and calcined at 600° C. for 5 h to obtain a silica-alumina material P-1. The properties of the silica-alumina material P-1 are shown in Table 1.

According to the SEM image (FIG. 1), the silica-alumina material comprises a lamellar structure and a non-lamellar structure, and the average particle size of the silica-alumina material is 50 nm. The average length of the lamellar structure is 1.0 μm, the average thickness of the lamellar structure is 50 nm, and the lamellar structure accounts for 35% of the total volume of the silica-alumina material. According to the measurement, the $SiO_2/Al_2O_3$ molar ratio of the silica-alumina material is 1.21. In addition, the XRD pattern of the calcined form of the silica-alumina material is shown in FIG. 2, which shows a crystal structure. Meanwhile, each diffraction peak gradually grows stronger with the increase of the time of the hydrothermal treatment (the above is h1=8 hours and the below is h2=16 hours), indicating that the proportion of the lamellar structure in the silica-alumina material is gradually increased. In the Si-NMR spectrum (FIG. 3) of the silica-alumina material, an absorption peak is present at a chemical shift of around −87 ppm, and the absorption peak gradually grows stronger with the increase of the time of the hydrothermal treatment (h1=8 hours, h2=16 hours). In the Al-NMR spectrum (FIG. 4) of the above-mentioned silica-alumina material, an absorption peak is present at a chemical shift of around 57 ppm, and the absorption peak gradually grows stronger with the increase of the time of the hydrothermal treatment (h1=8 hours, h2=16 hours). The calcined form of the silica-alumina material shows no diffraction peak in a small-angle XRD pattern (FIG. 5).

(2) Production of Hydrogenation Catalyst 500 g of the prepared PO-1 silica-alumina dry sample was taken, 10 g of *sesbania* powder, 12.15 g of citric acid and 420 g of water were added thereto, uniformly mixed, then pelletized, and the pelletized sample was calcined at 650° C. for 4 h to obtain a carrier Z1 having a particle size of 0.3-0.8 mm.

28.57 g of phosphoric acid was weighed, 800 mL of distilled water was added, then 77.58 g of molybdenum oxide and 35.56 g of basic nickel carbonate were added sequentially, heated and stirred until completely dissolved, and the volume of the solution was adjusted to 1000 mL using distilled water to obtain a solution L1. The carrier Z1 was subjected to saturated impregnation with the solution L1, dried at 110° C. for 2 h, and calcined at 450° C. for 3 h to obtain a catalyst C1, the properties of which are shown in Table 2.

Example 2

This example was carried out under the same conditions as in Example 1, except that: the silica sol was changed to a water glass solution, the concentration was adjusted to 58 g $SiO_2$/L, the flow rate of the mixed liquor A was 15 mL/min, the deionized water in the reactor was heated to 80° C. to obtain a silica-alumina dry sample PO-2, and calcined at 600° C. for 5 hours to obtain a silica-alumina material P-2. The properties of the resulted material are shown in Table 1.

The silica-alumina material has a $SiO_2/Al_2O_3$ molar ratio of 1.44, and comprises a lamellar structure with an average length of 1.5 μm and an average thickness of 61 nm. The lamellar structure accounts for 54% of the total volume of the silica-alumina material.

500 g of the prepared PO-2 silica-alumina dry sample was taken, 21.4 g of acetic acid (85 wt %) and 410 g of water were added thereto, uniformly mixed, then pelletized, and the pelletized sample was calcined at 600° C. for 5 hours to obtain a carrier Z2 having a particle size of 0.3-0.8 mm.

The carrier Z2 was subjected to saturated impregnation with the solution L1, dried at 110° C. for 2 h, and calcined at 580° C. for 3 h to obtain a catalyst C2, the properties of which are shown in Table 2.

Example 3

This example was carried out under the same conditions as in Example 1, except that: the pH value of the reaction was controlled to 9.0 by adjusting the flow rate of sodium metaaluminate, 53 g of sodium carbonate was added into the reactor under stirring to adjust the pH value to 11.0, the treatment temperature was 280° C. and the treatment pressure was 0.4 MPa to obtain a silica-alumina dry sample PO-3, and calcined at 600° C. for 5 hours to obtain a silica-alumina material P-3. The properties of the resulted material are shown in Table 1.

The silica-alumina material has a $SiO_2/Al_2O_3$ molar ratio of 1.19, and comprises a lamellar structure with an average length of 1.4 μm and an average thickness of 56 nm. The lamellar structure accounts for 40% of the total volume of the silica-alumina material.

500 g of the prepared PO-3 silica-alumina dry sample was taken, 10.0 g of methyl cellulose and 450 g of water were added thereto, uniformly mixed, then pelletized, and the pelletized sample was calcined at 600° C. for 5 hours to obtain a carrier Z3 having a particle size of 0.3-0.8 mm.

The carrier Z3 was subjected to saturated impregnation with the solution L1, dried at 110° C. for 2 h, and calcined at 480° C. for 4 h to obtain a catalyst C3, the properties of which are shown in Table 2.

Example 4

This example was carried out under the same conditions as in Example 1, except that: the acidification with 1 mol/L dilute sulfuric acid solution was not performed, a silica-alumina dry sample PO-4 was obtained and calcined for 5 hours at 600° C. to obtain a silica-alumina material P-4. The properties of the resulted material are shown in Table 1.

500 g of the prepared PO-4 silica-alumina dry sample was taken, 10 g of *sesbania* powder, 12.15 g of citric acid and 420 g of water were added thereto, uniformly mixed, then pelletized, and the pelletized sample was calcined at 650° C. for 4 h to obtain a carrier Z4 having a particle size of 0.3-0.8 mm.

The carrier Z4 was subjected to saturated impregnation with the solution L1, dried at 110° C. for 2 h, and calcined at 450° C. for 3 h to obtain a catalyst C4, the properties of which are shown in Table 2.

The silica-alumina material has a $SiO_2/Al_2O_3$ molar ratio of 1.19, and comprises a lamellar structure with an average length of 1.5 μm and an average thickness of 32 nm. The lamellar structure accounts for 15% of the total volume of the silica-alumina material.

Example 5

This example was carried out under the same conditions as in Example 1, except that: the causticity ratio of sodium metaaluminate was adjusted to 1.20, the pH for gelling was adjusted to 6.0, a silica-alumina dry sample PFO-5 was obtained, and calcined at 600° C. for 5 hours to obtain a silica-alumina material P-5. The properties of the resulted material are shown in Table 1.

500 g of the prepared PO-5 silica-alumina dry sample was taken, 10 g of *sesbania* powder, 12.15 g of citric acid and 420 g of water were added thereto, uniformly mixed, then pelletized, and the pelletized sample was calcined at 650° C. for 4 h to obtain a carrier Z5 having a particle size of 0.3-0.8 mm.

The carrier Z5 was subjected to saturated impregnation with the solution L1, dried at 110° C. for 2 h, and calcined at 450° C. for 3 h to obtain a catalyst C5, the properties of which are shown in Table 2.

The silica-alumina material has a $SiO_2/Al_2O_3$ molar ratio of 1.19, and comprises a lamellar structure with an average length of 1.0 μm and an average thickness of 20 nm. The lamellar structure accounts for 10% of the total volume of the silica-alumina material.

Example 6

This example was carried out under the same conditions as in Example 1, except that: the water-soluble carbonate was changed to sodium hydroxide to obtain a silica-alumina dry sample PFO-6, and calcined at 600° C. for 5 hours to obtain a silica-alumina material P-6. The properties of the resulted material are shown in Table 1.

500 g of the prepared PO-6 silica-alumina dry sample was taken, 10 g of *sesbania* powder, 12.15 g of citric acid and 420 g of water were added thereto, uniformly mixed, then pelletized, and the pelletized sample was calcined at 650° C. for 4 h to obtain a carrier Z6 having a particle size of 0.3-0.8 mm.

The carrier Z6 was subjected to saturated impregnation with the solution L1, dried at 110° C. for 2 h, and calcined at 450° C. for 3 h to obtain a catalyst C6, the properties of which are shown in Table 2.

The silica-alumina material has a $SiO_2/Al_2O_3$ molar ratio of 1.19, and comprises a lamellar structure with an average length of 0.8 μm and an average thickness of 15 nm. The lamellar structure accounts for ≤5% of the total volume of the silica-alumina material.

Example 7

This example was carried out under the same conditions as in Example 1, except that: the adjustment of the pH value with the water-soluble carbonate was not performed, a silica-alumina dry sample PFO-7 was obtained, and calcined at 600° C. for 5 h to obtain a silica-alumina material P-7. The properties of the resulted material are shown in Table 1.

500 g of the prepared PO-7 silica-alumina dry sample was taken, 10 g of *sesbania* powder, 12.15 g of citric acid and 420 g of water were added thereto, uniformly mixed, then pelletized, and the pelletized sample was calcined at 650° C. for 4 h to obtain a carrier Z7 having a particle size of 0.3-0.8 mm.

The carrier Z7 was subjected to saturated impregnation with the solution L1, dried at 110° C. for 2 h, and calcined at 450° C. for 3 h to obtain a catalyst C7, the properties of which are shown in Table 2.

The silica-alumina material has a $SiO_2/Al_2O_3$ molar ratio of 1.19, but no lamellar structure is formed.

Example 8

This example was carried out under the same conditions as in Example 1, except that: ammonium carbonate was added to adjust the pH value to 9.5, a silica-alumina dry sample PFO-8 was obtained, and calcined at 600° C. for 5 hours to obtain a silica-alumina material P-7. The properties of the resulted material are shown in Table 1.

500 g of the prepared PO-8 silica-alumina dry sample was taken, 10 g of *sesbania* powder, 12.15 g of citric acid and 420 g of water were added thereto, uniformly mixed, then pelletized, and the pelletized sample was calcined at 650° C. for 4 h to obtain a carrier Z8 having a particle size of 0.3-0.8 mm.

The carrier Z8 was subjected to saturated impregnation with the solution L1, dried at 110° C. for 2 h, and calcined at 450° C. for 3 h to obtain a catalyst C8, the properties of which are shown in Table 2.

The silica-alumina material has a $SiO_2/Al_2O_3$ molar ratio of 1.20, and comprises a lamellar structure with an average length of 0.6 μm and an average thickness of 20 nm. The lamellar structure accounts for 3% of the total volume of the silica-alumina material.

Example 9

(1) Production of Silica-Alumina Material

An aluminum sulfate solution with a concentration of 60 g $Al_2O_3$/L, a water glass solution with a concentration of 75 g $SiO_2$/L and a modulus of 3.0 were prepared for further use, and a dilute nitric acid solution with a concentration of 2 mol/L was prepared for further use. A sodium metaaluminate solution with a caustic ratio of 1.30 and a concentration of 130 g $Al_2O_3$/L was prepared for further use.

1.4 L of a silica sol solution with a concentration of 80 g $SiO_2$/L was measured and added into a container, and 1 L of the aluminum sulfate solution with a concentration of 60 g $Al_2O_3$/L was slowly added under stirring, during which process aluminum hydroxide colloid was generated, but the solution was still present as a liquid. Then, the 2 mol/L dilute nitric acid solution was added, the pH value was adjusted to 4.0, and an acidification treatment was performed to obtain a mixed liquor A.

1000 mL of deionized water was added as bottom water into a 5000 mL reactor, stirring and heating were started, the deionized water was heated to 60° C., the mixed liquor A was added into the reactor at a rate of 20 mL/min, the prepared sodium metaaluminate solution was added concurrently at the same time, the pH value of the reaction was controlled to 9.5 by adjusting the flow rate of the sodium metaaluminate solution, and the temperature and the pH value of the slurry in the reactor were kept constant. After the reaction was completed, the amount of sodium metaaluminate added was 620 mL, and 84 g of ammonium bicarbonate was added into the reactor under stirring to adjust the pH value to 11.0. The slurry was charged into a reactor and treated for 10 hours under stirring, the treatment temperature was 230° C., and the treatment pressure was 0.5 MPa. The treated slurry was washed with hot water at 90° C. until the liquid was neutral, dried at 150° C. for 4 h to obtain a dry sample PFO-9, and calcined at 600° C. for 5 h to obtain a silica-alumina material P-9. The properties of the resulted material are shown in Table 1.

The silica-alumina material has a $SiO_2/Al_2O_3$ molar ratio of 1.35, and comprises a lamellar structure with an average length of 1.44 μm and an average thickness of 59 nm. The lamellar structure accounts for 48% of the total volume of the silica-alumina material.

(2) Production of Hydrogenation Catalyst 500 g of the prepared PFO-9 silica-alumina dry sample was taken, 7 g of *sesbania* powder, 31.3 g of nitric acid (65 wt %) and 410 g of water were added thereto, uniformly mixed, then pelletized, and the pelletized sample was calcined at 550° C. for 5 hours to obtain a carrier Z9 having a particle size of 0.3-0.8 mm.

78.88 g of phosphoric acid was weighed, 800 mL of distilled water was added, 185.68 g of molybdenum oxide and 50.81 g of basic cobalt carbonate were added sequentially, heated and stirred until completely dissolved, and the solution was adjusted to 2000 mL using distilled water to obtain a solution L2. The carrier Z9 was subjected to saturated impregnation with the solution L2, dried at 110° C. for 4 h, and calcined at 500° C. for 3 h to obtain a catalyst C9, the properties of which are shown in Table 2.

Example 10

This example was carried out under the same conditions as in Example 4, except that: 600 mL of water was added into the reactor, the gelling temperature was adjusted to 80° C., the pH value was adjusted to 10.0, 20 g of sodium carbonate was added into the slurry after gelling to adjust the pH value to 10.5, the treatment temperature was 280° C., the treatment pressure was 0.4 MPa, a silica-alumina dry sample PFO-10 was obtained, and calcined at 600° C. for 5 hours, to obtain a silica-alumina material PF-10. The properties of the resulted material are shown in Table 1.

The silica-alumina material has a $SiO_2/Al_2O_3$ molar ratio of 1.34, and comprises a lamellar structure with an average length of 1.41 μm and an average thickness of 58 nm. The lamellar structure accounts for 44% of the total volume of the silica-alumina material.

500 g of the prepared PFO-10 silica-alumina dry sample was taken, 15 g of *sesbania* powder and 470 g of water were added thereto, uniformly mixed, then pelletized, and the pelletized sample was calcined at 750° C. for 3 h to obtain a carrier Z10 having a particle size of 0.3-0.8 mm.

The carrier Z10 was subjected to saturated impregnation with the solution L2, dried at 110° C. for 2 h, and calcined at 550° C. for 3 h to obtain a catalyst C10, the properties of which are shown in Table 2.

Comparative Example 1

(1) Production of Silica-Alumina Material

An aluminum sulfate solution with a concentration of 50 g $Al_2O_3$/L and a silica sol solution with a concentration of 50 g $SiO_2$/L and a modulus of 2.8 were prepared for further use, and a sodium metaaluminate solution with a causticity ratio of 1.25 and a concentration of 160 g $Al_2O_3$/L was prepared for further use.

700 mL of deionized water was added as bottom water into a 5000 mL reactor, stirring and heating were started, the deionized water was heated to 80° C., the aluminum sulfate was added at 25 mL/min and the silica sol was added at 28 mL/min into the reactor, the prepared sodium metaaluminate solution was added concurrently at the same time, the pH value of the reaction was controlled to 8.3 by adjusting the flow rate of the sodium metaaluminate solution, and the temperature and the pH value of the slurry in the reactor were kept constant. After the reaction was completed, the amount of sodium metaaluminate added was 325 mL, and 75 g of ammonium carbonate was added into the reactor under stirring to adjust the pH value to 10.8. The slurry was charged into a reactor and treated for 8 hours (corresponding to Δt+6 hours) with stirring at a treatment temperature of 210° C. and a treatment pressure of 0.4 MPa. The treated slurry was washed with hot water at 90° C. until the liquid was neutral, dried at 120° C. for 6 h to obtain a dry sample PFO-1, and calcined at 600° C. for 5 h to obtain a silica-alumina material PF-1. The properties of the resulted material are shown in Table 1.

The silica-alumina material has a $SiO_2/Al_2O_3$ molar ratio of 1.20, and no lamellar structure but only non-lamellar structure can be observed from the SEM image.

(2) Production of Hydrogenation Catalyst 500 g of the prepared PFO-1 silica-alumina dry sample was taken, 10 g of *sesbania* powder, 12.15 g of citric acid and 420 g of water were added thereto, uniformly mixed, then pelletized, and the pelletized sample was calcined at 650° C. for 4 hours to obtain a carrier ZF1 having a particle size of 0.3-0.8 mm.

The carrier ZF1 was subjected to saturated impregnation with the solution L1, dried at 110° C. for 2 h, calcined at 450° C. for 3 h to obtain a catalyst CF1, the properties of which are shown in Table 2.

Comparative Example 2

(1) Production of Silica-Alumina Material

An aluminum sulfate solution with a concentration of 50 g $Al_2O_3$/L and a silica sol solution with a concentration of 50 g $SiO_2$/L and a modulus of 2.8 were prepared for further use, and a dilute sulfuric acid solution with a concentration of 1 mol/L was prepared for further use. A sodium metaaluminate solution with a causticity ratio of 1.25 and a concentration of 160 g $Al_2O_3$/L was prepared for further use.

1 L of the aluminum sulfate solution with a concentration of 50 g $Al_2O_3$/L was measured and charged into a container, 1.44 L of the silica sol solution with a concentration of 50 g $SiO_2$/L was slowly added under stirring, during which a large amount of aluminum hydroxide gel was generated, causing a poor fluidity, then the 1 mol/L dilute sulfuric acid solution was added, the pH value was adjusted to 3.5, and an acidification treatment was performed to obtain a mixed liquor A.

700 mL of deionized water was added as bottom water into a 5000 mL reactor, stirring and heating were started, the deionized water was heated to 80° C., the mixed liquor A was added into the reactor at a rate of 28 mL/min, the prepared sodium metaaluminate solution was added concurrently at the same time, the pH value of the reaction was controlled to 8.3 by adjusting the flow rate of the sodium metaaluminate solution, and the temperature and the pH value of the slurry in the reactor were kept constant. After the reaction was completed, the amount of sodium metaaluminate added was 325 mL, and 75 g of ammonium carbonate was added into the reactor under stirring to adjust the pH value to 10.8. The slurry was charged into a reactor and treated for 8 hours (corresponding to Δt+6 hours) with stirring at a treatment temperature of 210° C. and a treatment pressure of 0.4 MPa. The treated slurry was washed with hot water at 90° C. until the liquid was neutral, dried at 120° C. for 6 h to obtain a dry sample PFO-2, and calcined at 600° C. for 5 h to obtain a silica-alumina material PF-2. The properties of the resulted material are shown in Table 1.

(2) Production of Hydrogenation Catalyst 500 g of the prepared PFO-2 silica-alumina dry sample was taken, 10 g of *sesbania* powder, 12.15 g of citric acid and 420 g of water were added thereto, uniformly mixed, then pelletized, and the pelletized sample was calcined at 650° C. for 4 hours to obtain a carrier ZF2 having a particle size of 0.3-0.8 mm.

The carrier ZF2 was subjected to saturated impregnation with the solution L1, dried at 110° C. for 2 h, calcined at 450° C. for 3 h to obtain a catalyst CF2, the properties of which are shown in Table 2.

The silica-alumina material has a $SiO_2/Al_2O_3$ molar ratio of 1.19, and no lamellar structure but only non-lamellar structure can be observed from the SEM image.

Comparative Example 3

(1) Production of Silica-Alumina Material

An aluminum sulfate solution with a concentration of 50 g $Al_2O_3$/L and a silica sol solution with a concentration of 50 g $SiO_2$/L and a modulus of 2.8 were prepared for further use, and a dilute sulfuric acid solution with a concentration of 1 mol/L was prepared for further use. A sodium metaaluminate solution with a causticity ratio of 1.25 and a concentration of 160 g $Al_2O_3$/L was prepared for further use.

1.44 L of the silica sol solution with a concentration of 50 g $SiO_2$/L was measured and added into a container, and 1 L of the aluminum sulfate solution with a concentration of 50 g $Al_2O_3$/L was slowly added under stirring, during which process aluminum hydroxide colloid was generated, but the solution was still present as a liquid. Then, the 1 mol/L dilute sulfuric acid solution was added, the pH value was adjusted to 3.5, and an acidification treatment was performed to obtain a mixed liquor A.

700 mL of deionized water was added as bottom water into a 5000 mL reactor, stirring and heating were started, the deionized water was heated to 80° C., the mixed liquor A was added into the reactor at a rate of 28 mL/min, the prepared sodium metaaluminate solution was added concurrently at the same time, the pH value of the reaction was controlled to 8.3 by adjusting the flow rate of the sodium metaaluminate solution, and the temperature and the pH value of the slurry in the reactor were kept constant. After the reaction was completed, the amount of sodium metaaluminate added was 325 mL, and 75 g of ammonium carbonate was added into the reactor under stirring to adjust the pH value to 10.8. The slurry was charged into a reactor, washed with hot water at 90° C. until the liquid was neutral, dried at 120° C. for 6 hours to obtain a dry sample PFO-1, and calcined at 600° C. for 5 hours to obtain a silica-alumina material PF-3. The properties of the resulted material are shown in Table 1.

The silica-alumina material has a $SiO_2/Al_2O_3$ molar ratio of 1.20, and no lamellar structure but only non-lamellar structure can be observed from the SEM image.

(2) Production of Hydrogenation Catalyst 500 g of the prepared PFO-3 silica-alumina dry sample was taken, 10 g of *sesbania* powder, 12.15 g of citric acid and 420 g of water were added thereto, uniformly mixed, then pelletized, and the pelletized sample was calcined at 650° C. for 4 hours to obtain a carrier ZF3 having a particle size of 0.3-0.8 mm.

The carrier ZF3 was subjected to saturated impregnation with the solution L1, dried at 110° C. for 2 h, calcined at 450° C. for 3 h to obtain a catalyst CF3, the properties of which are shown in Table 2.

Comparative Example 4

(1) Production of Silica-Alumina Material

An aluminum sulfate solution with a concentration of 50 g $Al_2O_3$/L and a silica sol solution with a concentration of 50 g $SiO_2$/L and a modulus of 2.8 were prepared for further use, and a dilute sulfuric acid solution with a concentration of 1 mol/L was prepared for further use. A sodium metaaluminate solution with a causticity ratio of 1.25 and a concentration of 160 g $Al_2O_3$/L was prepared for further use.

1.44 L of the silica sol solution with a concentration of 50 g $SiO_2$/L was measured and added into a container, 325 mL of the sodium metaaluminate solution was slowly added under stirring, then the 1 mol/L dilute sulfuric acid solution was added, the pH value was adjusted to 3.5, during which a large amount of aluminum hydroxide gel was generated, causing a poor fluidity, and a suspension A was obtained.

1 L of the aluminum sulfate solution with a concentration of 50 g $Al_2O_3$/L, during which process aluminum hydroxide colloid was generated, but the solution was still present as a liquid. Then, the 1 mol/L dilute sulfuric acid solution was added, the pH value was adjusted to 3.5, and an acidification treatment was performed to obtain a mixed liquor A.

700 mL of deionized water was added as bottom water into a 5000 mL reactor, stirring and heating were started, the deionized water was heated to 80° C., adding the suspension A into the reactor at 28 mL/min, 1 L of the prepared aluminum sulfate solution with a concentration of 50 g $Al_2O_3$/L was added concurrently at the same time, the pH value of the reaction was controlled to 8.3 by adjusting the flow rate of the sodium metaaluminate solution, and the temperature and the pH value of the slurry in the reactor were kept constant. After the reaction was completed, 75 g of ammonium carbonate was added to the reactor under stirring to adjust the pH to 10.8. The slurry was charged into a reactor and treated for 8 hours (corresponding to Δt+6 hours) with stirring at a treatment temperature of 210° C. and a treatment pressure of 0.4 MPa. The treated slurry was washed with hot water at 90° C. until the liquid was neutral, dried at 120° C. for 6 h to obtain a dry sample PF0-4, and calcined at 600° C. for 5 h to obtain a silica-alumina material PF-4. The properties of the resulted material are shown in Table 1.

The molar ratio of $SiO_2/Al_2O_3$ of the silica-alumina material is 1.20, and no lamellar structure but only non-lamellar structure can be observed from the SEM image.

(2) Production of Hydrogenation Catalyst 500 g of the prepared PFO-4 silica-alumina dry sample was taken, 10 g of *sesbania* powder, 12.15 g of citric acid and 420 g of water were added thereto, uniformly mixed, then pelletized, and the pelletized sample was calcined at 650° C. for 4 hours to obtain a carrier ZF4 having a particle size of 0.3-0.8 mm.

28.57 g of phosphoric acid was weighed, 800 mL of distilled water was added, then 77.58 g of molybdenum oxide and 35.56 g of basic nickel carbonate were added sequentially, heated and stirred until completely dissolved, and the volume of the solution was adjusted to 1000 mL using distilled water to obtain a solution L1. The carrier ZF4 was subjected to saturated impregnation with the solution L1, dried at 110° C. for 2 h, calcined at 450° C. for 3 h to obtain a catalyst CF4, the properties of which are shown in Table 2.

Comparative Example 5

(1) Production of Silica-Alumina Material

An aluminum sulfate solution with a concentration of 50 g $Al_2O_3$/L and a silica sol solution with a concentration of 50 g $SiO_2$/L and a modulus of 2.8 were prepared for further use, and a dilute sulfuric acid solution with a concentration of 1 mol/L was prepared for further use. A sodium metaaluminate solution with a causticity ratio of 1.25 and a concentration of 160 g $Al_2O_3$/L was prepared for further use.

1.44 L of the silica sol solution with a concentration of 50 g $SiO_2$/L was measured and added into a container, and 1 L of the aluminum sulfate solution with a concentration of 50 g $Al_2O_3$/L was slowly added under stirring, during which process aluminum hydroxide colloid was generated, but the solution was still present as a liquid. Then, the 1 mol/L dilute sulfuric acid solution was added, the pH value was adjusted to 3.5, and an acidification treatment was performed to obtain a mixed liquor A.

The mixed liquor A was added into a 5000 mL reactor at a rate of 28 mL/min, the prepared sodium metaaluminate solution was added concurrently at the same time, the pH value of the reaction was controlled to 8.3 by adjusting the flow rate of the sodium metaaluminate solution, and heated in a water bath to keep the temperature of the slurry in the reactor to 80° C. and keep the pH value constant. After the reaction was completed, the amount of sodium metaaluminate added was 325 mL, and 75 g of ammonium carbonate was added into the reactor under stirring to adjust the pH value to 10.8. The slurry was charged into a reactor and treated for 8 hours (corresponding to Δt+6 hours) with stirring at a treatment temperature of 210° C. and a treatment pressure of 0.4 MPa. The treated slurry was washed with hot water at 90° C. until the liquid was neutral, dried at 120° C. for 6 h to obtain a dry sample PFO-5, and calcined at 600° C. for 5 h to obtain a silica-alumina material PF-5. The properties of the resulted material are shown in Table 1.

The silica-alumina material has a $SiO_2/Al_2O_3$ molar ratio of 1.20.

(2) Production of Hydrogenation Catalyst 500 g of the prepared PFO-5 silica-alumina dry sample was taken, 10 g of *sesbania* powder, 12.15 g of citric acid and 420 g of water were added thereto, uniformly mixed, then pelletized, and the pelletized sample was calcined at 650° C. for 4 hours to obtain a carrier ZF5 having a particle size of 0.3-0.8 mm.

28.57 g of phosphoric acid was weighed, 800 mL of distilled water was added, then 77.58 g of molybdenum oxide and 35.56 g of basic nickel carbonate were added sequentially, heated and stirred until completely dissolved, and the volume of the solution was adjusted to 1000 mL using distilled water to obtain a solution L1. The carrier ZF5 was subjected to saturated impregnation with the solution L1, dried at 110° C. for 2 h, calcined at 450° C. for 3 h to obtain a catalyst CF5, the properties of which are shown in Table 2.

Comparative Example 6

(1) Production of Silica-Alumina Material

An aluminum sulfate solution with a concentration of 50 g $Al_2O_3$/L and a dilute sulfuric acid solution with a concentration of 1 mol/L were prepared for further use. A sodium metaaluminate solution with a causticity ratio of 1.25 and a concentration of 160 g $Al_2O_3$/L was prepared for further use.

72 g of white carbon black was weighed and added into a container, 1 L of the aluminum sulfate solution with a concentration of 50 g $Al_2O_3$/L was slowly added, and stirred to form a suspension. Then, the 1 mol/L dilute sulfuric acid solution was added to adjust the pH value to 3.5, and an acidification treatment was performed to obtain a suspension A.

700 mL of deionized water was added as bottom water into a 5000 mL reactor, stirring and heating were started, the deionized water was heated to 80° C., the mixed liquor A was added into the reactor at a rate of 28 mL/min, the prepared sodium metaaluminate solution was added concurrently at the same time, the pH value of the reaction was controlled to 8.3 by adjusting the flow rate of the sodium metaaluminate solution, and the temperature and the pH value of the slurry in the reactor were kept constant. After the reaction was completed, the amount of sodium metaaluminate added was 325 mL, and 75 g of ammonium carbonate was added into the reactor under stirring to adjust the pH value to 10.8. The slurry was charged into a reactor and treated for 8 hours (corresponding to Δt+6 hours) with stirring at a treatment temperature of 210° C. and a treatment pressure of 0.4 MPa. The treated slurry was washed with hot water at 90° C. until the liquid was neutral, dried at 120° C. for 6 h to obtain a dry sample PFO-6, and calcined at 600° C. for 5 h to obtain a silica-alumina material PF-6. The properties of the resulted material are shown in Table 1.

The silica-alumina material has a $SiO_2/Al_2O_3$ molar ratio of 1.20, and no lamellar structure can be observed from the SEM image.

Comparative Example 7

(1) Production of Silica-Alumina Material

An aluminum sulfate solution with a concentration of 50 g $Al_2O_3$/L and a silica sol solution with a concentration of 50 g $SiO_2$/L and a modulus of 2.8 were prepared for further use, and a dilute sulfuric acid solution with a concentration of 1 mol/L was prepared for further use. A sodium metaaluminate solution with a causticity ratio of 1.25 and a concentration of 160 g $Al_2O_3$/L was prepared for further use.

1.44 L of the silica sol solution with a concentration of 50 g $SiO_2$/L was measured and added into a container, and 1 L of the aluminum sulfate solution with a concentration of 50 g $Al_2O_3$/L was slowly added under stirring, during which process aluminum hydroxide colloid was generated, but the solution was still present as a liquid. Then, the 1 mol/L dilute sulfuric acid solution was added, the pH value was adjusted to 3.5, and an acidification treatment was performed to obtain a mixed liquor A.

700 mL of deionized water was added as bottom water into a 5000 mL reactor, stirring and heating were started, the deionized water was heated to 80° C., the mixed liquor A was added into the reactor at a rate of 28 mL/min, the prepared sodium metaaluminate solution was added concurrently at the same time, the pH value of the reaction was controlled to 8.3 by adjusting the flow rate of the sodium metaaluminate solution, and the temperature and the pH value of the slurry in the reactor were kept constant. After the reaction was completed, the amount of sodium metaaluminate added was 325 mL, and 75 g of ammonium carbonate was added into the reactor under stirring to adjust the pH value to 10.8. The slurry was charged into a reactor and treated for 3 hours (corresponding to Δt+1 hour) with stirring at a treatment temperature of 210° C. and a treatment pressure of 0.4 MPa. The treated slurry was washed with hot water at 90° C. until the liquid was neutral, dried at 120° C. for 6 h to obtain a dry sample PFO-7, and calcined at 600° C. for 5 h to obtain a silica-alumina material PF-7. The properties of the resulted material are shown in Table 1.

The silica-alumina material has a $SiO_2/Al_2O_3$ molar ratio of 1.20, and comprises a lamellar structure with an average length of 0.85 μm and an average thickness of 25 nm. The lamellar structure accounts for 2% of the total volume of the silica-alumina material.

(2) Production of Hydrogenation Catalyst 500 g of the prepared PFO-7 silica-alumina dry sample was taken, 10 g of *sesbania* powder, 12.15 g of citric acid and 420 g of water were added thereto, uniformly mixed, then pelletized, and the pelletized sample was calcined at 650° C. for 4 hours to obtain a carrier Z7 having a particle size of 0.3-0.8 mm.

The carrier Z7 was subjected to saturated impregnation with the solution L1, dried at 110° C. for 2 h, and calcined at 450° C. for 3 h to obtain a catalyst CF7, the properties of which are shown in Table 2.

TABLE 1

Properties of the silica-alumina materials (examples)

| | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Pore volume, mL/g | 1.28 | 1.34 | 1.30 | 0.95 | 0.88 | 1.00 | 0.91 | 0.98 | 1.36 | 1.21 |
| Specific surface area, m²/g | 284 | 269 | 276 | 274 | 296 | 301 | 316 | 311 | 274 | 288 |
| Average pore diameter/nm | 18.01 | 19.90 | 18.84 | 13.86 | 11.89 | 13.26 | 11.50 | 12.58 | 19.83 | 16.80 |
| Pore distribution, % | | | | | | | | | | |
| <10 nm | 2.98 | 2.18 | 2.36 | 5.06 | 18.41 | 6.87 | 10.14 | 7.23 | 2.08 | 3.42 |
| 10-50 nm | 79.57 | 77.51 | 79.15 | 84.62 | 71.36 | 77.79 | 80.92 | 79.23 | 78.60 | 79.57 |
| >50 nm | 17.45 | 20.31 | 18.49 | 10.32 | 10.23 | 15.34 | 8.94 | 13.54 | 19.32 | 17.01 |
| Na₂O, wt % | 0.02 | 0.03 | 0.02 | 0.10 | 0.06 | 0.04 | 0.03 | 0.03 | 0.02 | 0.03 |
| SiO₂/Al₂O₃ molar ratio | 1.21 | 1.44 | 1.19 | 1.19 | 1.19 | 1.20 | 1.20 | 1.19 | 1.35 | 1.34 |
| B acid, mmol/g | 0.164 | 0.189 | 0.170 | 0.08 | 0.07 | 0.146 | 0.110 | 0.132 | 0.169 | 0.149 |
| B/L | 0.639 | 0.687 | 0.671 | 0.364 | 0.313 | 0.531 | 0.412 | 0.508 | 0.651 | 0.639 |

TABLE 1

Properties of the silica-alumina material (comparative examples)

| | Comp. Ex. 1 | Comp. Ex. 2 | Comp. Ex. 3 | Comp. Ex. 4 | Comp. Ex. 5 | Comp. Ex. 6 | Comp. Ex. 7 |
|---|---|---|---|---|---|---|---|
| Pore volume, mL/g | 0.86 | 0.23 | 0.70 | 0.35 | 0.90 | 0.48 | 1.15 |
| Specific surface area, m²/g | 271 | 84 | 218 | 143 | 241 | 210 | 296 |
| Average pore diameter/nm | 12.69 | 10.91 | 12.82 | 9.79 | 14.93 | 9.13 | 15.54 |
| Pore distribution, % | | | | | | | |
| <10 nm | 13.81 | 78.11 | 28.31 | 59.23 | 4.23 | 69.43 | 2.31 |
| 10-50 nm | 77.28 | 21.48 | 44.55 | 28.61 | 72.34 | 16.19 | 81.46 |
| >50 nm | 8.91 | 0.41 | 27.14 | 12.16 | 23.43 | 14.38 | 16.23 |
| Na₂O, wt % | 3.24 | 0.28 | 0.17 | 3.86 | 0.08 | 0.12 | 0.03 |
| SiO₂/Al₂O₃ molar ratio | 1.19 | 1.30 | 1.19 | 0.91 | 1.20 | 1.20 | 1.20 |
| B acid, mmol/g | 0.04 | 0.01 | 0.06 | 0.02 | 0.151 | 0.02 | 0.101 |
| B/L | 0.398 | 0.09 | 0.449 | 0.312 | 0.548 | 0.402 | 0.458 |

TABLE 2

Properties of the catalyst (examples)

| | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Specific surface area, m²/g | 201 | 192 | 194 | 171 | 182 | 188 | 192 | 187 | 194 | 153 |
| Pore volume, mL/g | 0.74 | 0.78 | 0.76 | 0.66 | 0.59 | 0.68 | 0.63 | 0.66 | 0.67 | 0.59 |
| Total acid, mmol/g | 0.512 | 0.556 | 0.531 | 0.342 | 0.302 | 0.412 | 0.398 | 0.402 | 0.564 | 0.423 |

TABLE 2-continued

Properties of the catalyst (examples)

| | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Catalyst composition, wt % | 14.7 | 15.9 | 15.6 | 15.4 | 12.9 | 14.4 | 13.1 | 14.0 | 13.8 | 15.4 |
| $MoO_3$ | 5.89 | 5.93 | 5.90 | 5.93 | 5.84 | 5.86 | 5.84 | 5.87 | 12.89 | 12.83 |
| NiO/CoO | 1.39 | 1.43 | 1.38 | 1.41 | 1.36 | 1.39 | 1.40 | 1.42 | 2.10 | 2.21 |
| P | 0.50 | 0.58 | 0.52 | 0.53 | 0.51 | 0.54 | 0.56 | 0.53 | 1.38 | 1.40 |
| Abrasion index, % | 0.48 | 0.51 | 0.50 | 0.56 | 0.53 | 0.51 | 0.49 | 0.47 | 0.45 | 0.48 |

TABLE 2

Properties of the catalyst (comparative examples)

| | Comp. Ex. 1 | Comp. Ex. 2 | Comp. Ex. 3 | Comp. Ex. 4 | Comp. Ex. 5 | Comp. Ex. 6 | Comp. Ex. 7 |
|---|---|---|---|---|---|---|---|
| Specific surface area, $m^2/g$ | 186 | 17 | 102 | 28 | 143 | 79 | 205 |
| Pore volume, mL/g | 0.51 | 0.08 | 0.35 | 0.12 | 0.52 | 0.15 | 0.70 |
| Total acid, mmol/g | 0.161 | 0.02 | 0.188 | 0.101 | 0.338 | 0.113 | 0.426 |
| Catalyst composition, wt % | | | | | | | |
| $MoO_3$ | 5.82 | 5.89 | 5.91 | 5.86 | 5.88 | 5.92 | 5.90 |
| NiO/CoO | 1.41 | 1.43 | 1.39 | 1.41 | 1.38 | 1.39 | 1.40 |
| P | 0.52 | 0.56 | 0.52 | 0.51 | 0.50 | 0.53 | 0.55 |
| Abrasion index, % | 3.87 | 2.17 | 1.89 | 4.65 | 0.60 | 0.64 | 0.53 |

The activity of the catalyst was evaluated in an autoclave, and the properties of the feedstock oil and the evaluation conditions were are in Table 3. The evaluation results compared to the activity of Comparative Example 1 are shown in Table 4, taking the activity of Comparative Example 1 as 100.

TABLE 3

Properties of the feedstock oil and the evaluation conditions

| Item | Value |
|---|---|
| Properties of feedstock oil | |
| Sulfur, % | 5.76 |
| Carbon residue, % | 24.86 |
| $Ni + V/\mu g \cdot g^{-1}$ | 214.38 |
| Yield of >500° C. residue oil, % | 93.2 |
| Process conditions | |
| Reaction temperature/° C. | 420 |
| Reaction pressure/MPa | 15 |
| Volume ratio of oil-to-reagent | 13:1 |
| Reaction time/h | 1 |

TABLE 4

Evaluation results of catalysts (examples)

| Relative hydrogenation activity | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| HDS | 162 | 173 | 168 | 136 | 132 | 138 | 136 | 138 | 206 | 196 |
| HDCCR | 140 | 144 | 141 | 119 | 116 | 121 | 120 | 122 | 179 | 174 |
| HD (Ni + V) | 182 | 196 | 193 | 128 | 118 | 123 | 121 | 126 | 151 | 159 |
| Relative conversion rate of >500° C. residual oil | 143 | 148 | 145 | 121 | 119 | 122 | 120 | 122 | 158 | 151 |

TABLE 5

Evaluation results of catalysts (comparative examples)

| Relative hydrogenation activity | Comp. Ex. 1 | Comp. Ex. 2 | Comp. Ex. 3 | Comp. Ex. 4 | Comp. Ex. 5 | Comp. Ex. 6 | Comp. Ex. 7 |
|---|---|---|---|---|---|---|---|
| HDS | 100 | 52 | 101 | 61 | 123 | 68 | 136 |
| HDCCR | 100 | 37 | 105 | 44 | 114 | 45 | 124 |
| HD (Ni + V) | 100 | 78 | 108 | 84 | 125 | 88 | 129 |
| Relative conversion rate of >500° C. residual oil | 100 | 90 | 104 | 93 | 113 | 94 | 136 |

As can be seen from the data in the tables: the silica-alumina material produced by the method of the present application has large pore volume, small proportion of <10 nm pores, low sodium oxide content and high B acid content. Compared with the catalyst obtained in comparative examples, the hydrogenation catalyst prepared using the silica-alumina material of the present application provides an improved impurity removal rate and residual oil conversion rate, and is particularly suitable for use as a heavy oil or residual oil hydrogenation catalyst.

The invention claimed is:

1. A silica-alumina material, having a $SiO_2/Al_2O_3$ molar ratio of from 0.8 to 1.5, comprising a lamellar structure having an average length of from 0.5 to 2 μm and an average thickness of from 30 to 80 nm, which in calcined form has an XRD pattern as shown in Table I or Table II below,

TABLE I

| 2θ | d-spacing (nm) | Relative strength |
|---|---|---|
| 14.0 | 0.12-0.13 | VS |
| 24.3 | 0.18-0.19 | VS |
| 34.3 | 0.07-0.08 | S |
| 42.6 | 0.11-0.13 | M |
| 51.9 | 0.10-0.13 | M |
| 66.4 | 0.06-0.08 | M |

TABLE II

| 2θ | d-spacing (nm) | Relative strength |
|---|---|---|
| 13.9 | 0.12-0.13 | VS |
| 24.2 | 0.17-0.18 | VS |
| 31 | 0.36-0.38 | M |
| 34.4 | 0.08-0.10 | S |
| 39.9 | 0.08-0.10 | M |
| 42.5 | 0.11-0.12 | M |
| 51.6 | 0.12-0.13 | W |
| 57.8 | 0.14-0.16 | W |
| 66.4 | 0.07-0.09 | W | where defining that the intensity value of the strongest diffraction peak in the XRD pattern is set to 100, then W means weak, i.e. relative intensity>0 to ≤20, M means medium, i.e. relative intensity>20 to ≤40, S means strong, i.e. relative intensity>40 to ≤60, and VS means very strong, i.e. relative intensity>60 to ≤100.

2. The silica-alumina material according to claim 1, having a pore volume of not less than 1.1 mL/g, and/or a specific surface area of 260-340 m²/g, and/or the pore volume of pores with a pore diameter of <10 nm accounts for ≤3% of the total pore volume, and/or the pore volume of pores with a pore diameter of 10-50 nm accounts for 70-85% of the total pore volume, and/or the pore volume of pores with a pore diameter of >50 nm accounts for 12-25% of the total pore volume, and/or an average pore diameter of 14-23 nm.

3. A silica-alumina material according to claim 1, having a Bronsted acid content of greater than 0.08 mmol/g and/or a ratio of Bronsted acid to Lewis acid of 0.2 to 0.8 and/or a Na₂O content of less than 0.2 wt % and/or an absorption peak at a chemical shift of −88 ppm to −94 ppm in its Si-NMR spectrum and an absorption peak at a chemical shift of around 57 ppm in its Al-NMR spectrum and/or showing no diffraction peak, when present in a calcined form, in its small-angle XRD pattern.

4. The silica-alumina material according to claim 1, further comprising a non-lamellar structure, wherein the lamellar structure accounts for 10-80% of a total volume of the silica-alumina material.

5. The silica-alumina material according to claim 1, wherein the silica-alumina material has a $SiO_2/Al_2O_3$ molar ratio of from 1.0 to 1.4, and/or the silica-alumina material comprises a lamellar structure having an average length of from 0.5 to 1.5 μm and an average thickness of from 30 to 75 nm, and/or the silica-alumina material is in calcined form having an XRD pattern as shown in FIG. 2.

6. The silica-alumina material according to claim 1, having a pore volume of 1.15-1.5 mL/g, and/or a specific surface area of 260-310 m²/g, and/or an average pore diameter of 16-21 nm.

7. A silica-alumina material according to claim 1, having a Bronsted acid content of 0.1 to 0.15 mmol/g, and/or a ratio of Bronsted acid to Lewis acid of 0.3 to 0.7.

8. A method for producing a silica-alumina material according to claim 1, comprising the following steps sequentially:
(1) adding an acidic aluminum source into a silicon source to obtain a mixture A,
(2) contacting said mixture A with an alkaline aluminum source in the presence of water to obtain a slurry B, and
(3) subjecting the slurry B to a hydrothermal treatment to obtain the silica-alumina material according to claim 1.

9. The method according to claim 8, wherein in step (1), the silicon source is a water-soluble or water-dispersible alkaline silicon-containing compound, and/or the silicon source is used in the form of an aqueous solution and a concentration of the silicon source, calculated as $SiO_2$, is 5 to 30 wt %, based on a total weight of the aqueous solution, and/or the acidic aluminum source is a water-soluble acidic aluminum-containing compound, and/or the acidic aluminum source is used in the form of an aqueous solution and a concentration of the acidic aluminum source, calculated as $Al_2O_3$, is 30-100 g/L, based on a total weight of the aqueous solution, and/or a weight ratio of the silicon source, calculated as $SiO_2$, to the acidic aluminum source, calculated as $Al_2O_3$, is 1:1 to 9:1.

10. The method according to claim 8, wherein in step (1), an acid is further added, and/or the acid is a water-soluble inorganic acid, and/or the acid is used in the form of an aqueous solution and a concentration of the acid is 2-6 wt %, based on a total weight of the aqueous solution, and/or the acid is added in such an amount that a pH of the mixture A is 2 to 4.

11. The method according to claim 8, wherein in step (2), the alkaline aluminum source is a water-soluble alkaline aluminum-containing compound, and/or the alkaline aluminum source is used in the form of an aqueous solution and the concentration of the alkaline aluminum source, calculated as $Al_2O_3$, is 130-350 g/L, based on a total weight of the aqueous solution, and/or based on a total volume of the mixture A, the alkaline aluminum source and water together, an amount of the mixture A used is 40-70 vol %, and/or based on a total volume of the mixture A, the alkaline aluminum source and water together, an amount of the alkaline aluminum source used is 20 to 40 vol %, and/or based on a total volume of the mixture A, the alkaline aluminum source and water together, an amount of water used is 10 to 20 vol %, and/or the mixture A and the alkaline aluminum source are added to the water sequentially or simultaneously, and/or the mixture A is added at a flow rate of 15 to 50 mL/min, and/or the alkaline aluminum source is added at a flow rate that is controlled to maintain a pH value of the slurry B at 7.5 to 10.5.

12. The method according to claim 8, wherein in step (2), a water-soluble carbonate is further added, and/or the water-soluble carbonate is selected from carbonates of one or more of alkali metals and ammonium, and/or the water-soluble carbonate is in solid form, and/or the water-soluble carbonate is added in such an amount that the pH of the slurry B is 10.5 to 12.

13. The method according to claim 8, wherein in step (3), the silica-alumina material is separated from the reaction system of the hydrothermal treatment, washed till neutral, and then dried, and/or drying conditions include: a drying temperature of 100-150° C., and a drying time of 6-10 hours.

14. The method according to claim 8, wherein in step (1), a temperature is from 25° C. to 50° C. and a pressure is normal pressure, and/or in step (2), a temperature is from 50° C. to 90° C. and a pressure is normal pressure, and/or in step (3), a temperature is from 180° C. to 300° C. and a pressure is from 0.1 MPa to 0.5 MPa, and/or in step (3), a time of the hydrothermal treatment is from $\Delta t+1$ to $\Delta t+20$ in unit h, wherein $\Delta t=t_{max}-t_0$, $t_0$ is an initial time of the hydrothermal treatment, and $t_{max}$ is a time at which the slurry B reaches a highest viscosity, and/or in step (3), the hydrothermal treatment is carried out for a period of time ranging from 6 to 20 h.

15. The method according to claim 8, wherein an auxiliary agent is further added, and/or the auxiliary agent is included in an amount of 1-8 wt %, calculated as oxide and relative to 100 wt % of a total weight of the silica-alumina material.

16. The method according to claim 8, wherein in step (1), the silicon source is one or more selected from water-soluble silicates, water glass, and silica sol, and/or a concentration of the silicon source, calculated as $SiO_2$, is 15 to 30 wt %, based on a total weight of the aqueous solution, and/or the acidic aluminum source is one or more selected from aluminum sulfate, aluminum nitrate, and aluminum chloride, and/or a concentration of the acidic aluminum source, calculated as $Al_2O_3$, is 30-80 g/L, based on a total weight of the aqueous solution, and/or a weight ratio of the silicon source, calculated as $SiO_2$, to the acidic aluminum source, calculated as $Al_2O_3$, is 1:1 to 7:1.

17. The method according to claim 8, wherein in step (1), the acidic aluminum source is added to the silicon source, and then an acid is added to obtain the mixture A, and/or the acid is one or more selected from sulfuric acid, nitric acid, and hydrochloric acid, and/or the concentration of the acid is 2-5 wt %, based on a total weight of the aqueous solution, and/or the acid is added in such an amount that a pH of the mixture is 3 to 4.

18. The method according to claim 8, wherein in step (2), the alkaline aluminum source is one or more selected from sodium metaaluminate and potassium metaaluminate, and/or a concentration of the alkaline aluminum source, calculated as $Al_2O_3$, is 150-250 g/L, based on a total weight of the aqueous solution, and/or based on a total volume of the mixture A, the alkaline aluminum source and water together, the amount of the mixture A used is 40-65 vol %, and/or based on a total volume of the mixture A, the alkaline aluminum source and water together, an amount of the alkaline aluminum source used is 25 to 40 vol %, and/or based on a total volume of the mixture A, the alkaline aluminum source and water together, an amount of water used is 13 to 20 vol %, and/or the mixture A and the alkaline aluminum source are added to the water concurrently, and/or the mixture A is added at a flow rate of 20 to 40 mL/min, and/or the alkaline aluminum source is added at a flow rate that is controlled to maintain a pH value of the slurry B at 8.5 to 10.5.

19. The method according to claim 8, wherein in step (2), the mixture A and the alkaline aluminum source are added to water, and then a water-soluble carbonate is added to obtain the slurry B, and/or the water-soluble carbonate is one or more selected from sodium carbonate, potassium carbonate, sodium bicarbonate, potassium bicarbonate, ammonium carbonate, ammonium bicarbonate, and/or the water-soluble carbonate is used in a solid form, and/or the water-soluble carbonate is added in such an amount that a pH of the slurry is 11 to 12.

20. The method according to claim 8, wherein in step (1), a temperature is from 25° C. to 40° C., and/or, in step (2), a temperature is from 50° C. to 80° C., and/or, in step (3), a temperature is from 180° C. to 250° C. and a pressure is from 0.1 MPa to 0.3 MPa, and/or, in step (3), a time of the hydrothermal treatment is from $\Delta t+4$ to $\Delta t+8$ in unit h, wherein $\Delta t=t_{max}-t_0$, $t_0$ is an initial time of the hydrothermal treatment, and $t_{max}$ is a time at which the slurry B reaches a highest viscosity, and/or, in step (3), the hydrothermal treatment is carried out for a period of time ranging from 8 to 12 h.

21. The method according to claim 8, wherein the auxiliary agent is one or more selected from phosphorus, boron and titanium, and/or the auxiliary agent is used in an amount of 2-6 wt %, calculated as oxide and relative to 100 wt % of a total weight of the silica-alumina material.

22. A catalytic material, comprising an active metal component and a silica-alumina material according to claim 1.

23. The catalytic material according to claim 22, wherein the active metal component is a metal component having hydrogenation activity, and/or the active metal component is present in an amount of 5-30 wt %, calculated as oxide and based on a total weight of the catalytic material.

24. The catalytic material according to claim 22, wherein the active metal component is at least one selected from the group consisting of Group VIB metals and Group VIII metals of the periodic table, and/or the active metal component is present in an amount of 5-25 wt %, calculated as oxide and based on a total weight of the catalytic material.

25. A hydrogenation process, comprising a step of subjecting a hydrocarbon-containing material to a hydrogenation reaction in the presence of the catalytic material according to claim 22.

* * * * *